United States Patent [19]
Hutchins et al.

[11] Patent Number: 5,502,561
[45] Date of Patent: Mar. 26, 1996

[54] CHARACTERIZATION OF PARTICLES BY MODULATED DYNAMIC LIGHT SCATTERING

[75] Inventors: Darrell K. Hutchins, Conway, Ark.; Barton E. Dahneke, Palmyra, N.Y.

[73] Assignee: Board of Trustees of the University of Arkansas, Little Rock, Ark.

[21] Appl. No.: 569,800

[22] Filed: Aug. 20, 1990

Related U.S. Application Data

[62] Division of Ser. No. 244,965, Sep. 15, 1988.

[51] Int. Cl.$^6$ .................................................. C01N 15/02
[52] U.S. Cl. ............................................. 356/336; 356/338
[58] Field of Search .................................. 356/28.5, 336, 356/338

[56] References Cited

U.S. PATENT DOCUMENTS 4,807,990  2/1989  Keefer ...................................... 356/28.5

FOREIGN PATENT DOCUMENTS 2453832  10/1975  Germany ................................ 356/338

OTHER PUBLICATIONS

Mazumder, M. K. "Laser Doppler Velocity Measurement Without Directional Ambiguity by Using Frequency Shifted Incident Beams" *Applied Physics Letters*, vol. 16, No. 11 (1 Jun. 1970) pp. 462–464.

Berne et al. *Dynamic Light Scattering* John Wiley & Sons, Inc. New York copyright 1976, pp. 53–88.

*Primary Examiner*—Richard A. Rosenberger
*Attorney, Agent, or Firm*—Edward Dugas

[57] ABSTRACT

A new class of methods for characterizing particles is described along with associated apparatuses. These methods are called modulated dynamic light scattering (MDLS) methods because they utilize time and space modulations of the incident or scattered light as well as modulations caused by random Brownian motions of the particles, for example, to measure particular properties. The autocorrelation function of the scattered light signal from a particle is measured to provide a highly resolved signature even when the signal is buried in noise. The dynamics of the scattered light signal from a suspended particle undergoing random Brownian translations and rotations is analyzed to obtain the relationship of the particle's properties to its autocorrelation function signature. By comparison of the theoretical and measured functions, properties of a particle suspended in a (1) liquid, (2) gas, or (3) rarefied gas can be determined. In cases (1) and (2) the general shape category, velocity, and translational friction coefficient of the particle and in case (3) these properties and the mass of the particle are determined. The particle charge and charge-to-mass ratio can also be determined in cases (2) and (3). In addition, other analytical techniques can also be used to determine information about the chemical and biological nature of the particle. Distributions of particles over one or more properties, singly or jointly, can then be precisely determined from a large number of individual particle measurements and particles of a species having a unique set of properties can be individually identified.

17 Claims, 7 Drawing Sheets

CHARACTERIZATION OF PARTICLES BY MODULATED DYNAMIC LIGHT SCATTERING

This is a division of application Ser. No. 244,965 filed Sep. 15, 1988.

TECHNICAL FIELD OF THE INVENTION

The present invention is directed to methods and apparatuses for determining several property values of at least one particle by utilizing the light or other radiation signal scattered from a particle in an intensity modulated illumination field or by utilizing the modulated scattered signal from at least one particle in a field of uniform illumination.

BACKGROUND OF THE INVENTION

Measurement of molecules and particles (simply denoted particles hereafter) by light scattering methods is frequently preferred over other methods because light scattering provides the advantages of convenient, fast, sensitive, non-destructive, in situ or even in vivo measurement. However, the inference of particle properties from static light scattering (SLS) signals can be extremely complex, depending strongly on particle index, size, shape and homogeneity, properties which are not generally known a priori. Measurement of particles by dynamic light scattering (DLS) techniques retains the advantages listed above while eliminating complexity in inferring properties including particle size and shape, since these inferences do not require detailed knowledge of the optical properties of the particles.

One strength of DLS techniques is their ability to measure a weighted mean value of a dynamic particle property (translational or rotational diffusion coefficient, electrophoretic mobility, . . . ) for a suspension of particles. However, this strength is sometimes a liability as the weighted mean value accessible is frequently not the one of interest and, except in special cases, the latter cannot be obtained from the former because these methods do not provide the distribution of particles over any property. Were a distribution provided, a number of moments of the distribution or the mean value of a number of properties of the suspension could be calculated.

Consider photon correlation spectroscopy (PCS) as an example of a DLS method. A PCS measurement of a suspension of spherical particles illuminated by a coherent light source provides, after some manipulation, the autocorrelation function of the electric field of the light signal scattered from the suspension. This function has the form of the Laplace transform of the product $A(\Gamma)F(\Gamma)$ $$C(\tau) = \int_0^\infty d\Gamma A(\Gamma) F(\Gamma) e^{-\Gamma \tau} \qquad (1)$$

where x is the delay time, $\Gamma = K^2 D$ the linewidth variable for a particle having diffusion coefficient $D = kT/f$, k the Boltzmann's constant, T the absolute temperature, $f = 3\pi\eta d$ the particle's friction coefficient, n the viscosity of the medium, d the particle diameter, K the magnitude of the scattering vector, $A(\Gamma)$ the light scattering cross-section and $F(\Gamma)$ the number distribution density (per unit $\Gamma$) of particles of linewidth $\Gamma$.

In principle, measured autocorrelation functions together with Equation (1) can be used to provide estimates of $F(\Gamma)$ which can be transformed into a size or other distribution function. However, precise extraction of $A(\Gamma)F(\Gamma)$ from Equation (1) is not trivial since this Fredholm integral equation of the first kind has the property that the $A(\Gamma)F(\Gamma)$ extracted is very sensitive to noise in $C(\tau)$. Moreover, because $A(\Gamma)$ is strongly dependent on particle size, the signal from any suspension of particles having significant breadth in its size distribution will be dominated by the signal from the fraction of particles having large $A(\Gamma)$ while the remaining particles contribute only slightly to $C(\tau)$. Finally, $C(\tau)$ dependence on other properties such as particle shape can also contribute to the imprecision with which a one-dimensional distribution can be determined since such dependence can lead to (apparent) noise in $C(\tau)$ and to the non-uniform weighting of $A(\Gamma)F(\Gamma)$ in Equation (1).

Because of these fundamental limitations in the PCS method in particular and in many DLS methods in general, improved methods are perused. The method of the present invention involves modulated dynamic light scattering (MDLS). In this method, a suspension of particles may be precisely characterized by individual measurement of many particles which provides precise distributions over one or more particles properties, singly or jointly. This strategy removes the limitations on precision associated with the inversion of a Fredholm integral equation, the simultaneous measurement of strong and weak signals and the measurement of particles distributed in an undetermined manner over additional properties. However, the methodology introduces its own limitations, namely, the longer time required to individually measure a large number of particles and the inability to measure particles that are too small to be individually detected. In spite of these limitations, the MDLS method will often provide more complete and precise information.

SUMMARY OF THE INVENTION

The method and apparatus of the present invention operates upon the signal, such as an electrical signal, derived from a suitable sensor that is positioned and oriented to detect the scattered signal from at least one particle illuminated by an acoustic or electromagnetic field suitably modulated such that the illumination intensity varies periodically in both time and space over a volume within which the particle(s) is measured.

The electrical signal is measured in time to obtain the time history of the signal or the sequence of time intervals at which some feature of the signal recurs or is processed to obtain the autocorrelation or other function of the signal in order to capture information in the frequency and amplitude modulation of the signal due to the translational and rotational motions of the particle(s).

The information so captured is used together with an appropriate analytical expression or analytical method to determine the mean square displacement ($\sigma^2$) of the particle in one dimension and the mean square rotations ($\sigma_r^2$s) of the particle about at least one of three mutually perpendicular axes through the particle as it depends on the delay time interval $\tau$. Since the $\sigma^2$ history depends on the time average value of the particle friction coefficient and, under certain conditions to be described below, the particle mass, the measured $\sigma^2$ history can be used to determine the particle friction coefficient and/or the particle mass. Likewise, since the $\sigma_r^2$ histories depend on the time average values of the rotational friction coefficients of the particle and, under the same certain conditions, the mass moments of inertia of the particle about the three axes, the measured $\sigma_r^2$ histories can be used to determine the particle rotational friction coefficients and/or mass moments of inertia about the three axes.

Moreover, a shape category of the particle is readily determined from the general form of the measured or processed signal such that the particle can be classified as to its general shape category, for example, spherical, slightly non-spherical, highly non-spherical, axisymmetric or non-axisymmetric.

Particle velocity is determined in the MDLS methods and apparatuses as well as the above mentioned properties. Measurement of particle or suspending fluid velocity is in itself a useful ability. Moreover, when an electrostatic field of known strength is imposed on the particle, the electrostatic charge and charge to mass ratio of the particle are determined.

Finally, additional analysis or processing of the scattered signal together with proper preparation of the sample particle when required provides information about the chemical, biological or structural nature of the particle.

It is a primary objective of the present invention to provide an improved method for characterizing particles.

It is another object of the present invention to provide a method for determining the particle mass, a method which is unlike others previously described in that it requires no assumptions regarding the shape, mass density, electrostatic charge, sedimentation velocity, light scattering cross-section or relationship of particle volume or mass and particle friction coefficient but provides the correct value of particle mass irrespective of any of these other properties and the velocity of their suspending fluid.

It is another object of the present invention to provide a dynamic light scattering method for characterizing particles.

It is a further object of the present invention to illuminate particles with at least one component of light having its intensity modulated periodically in both time and space to provide scattered light signals used to characterize the particles.

These and other objects of the present invention will become apparent when taken in conjunction with the following description and drawings, which drawings form a part of the present application and wherein like characters indicate like parts and which drawings form a part of the present specification.

DESCRIPTION OF THE PREFERRED EMBODIMENT

Figure 1A:
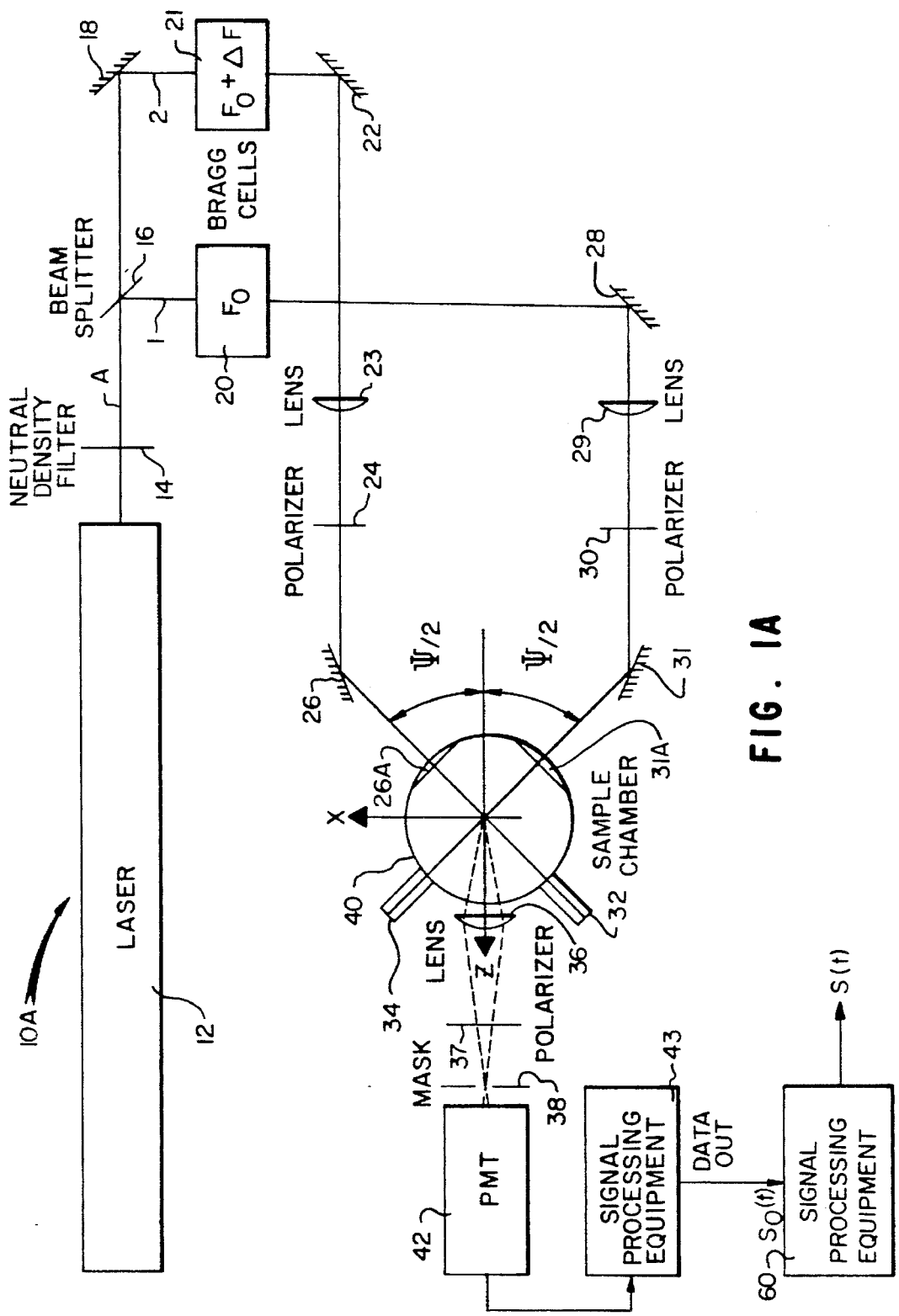
FIG. 1A is a block diagram of an MDLS device and associated signal processing equipment. This device illuminates a particle with light having one component (polarization or color) with a fringe pattern intensity field that is modulated to be periodic in both time and spatial displacements.

Illustrated in FIG. 1A is an MDLS device 10A which is used to illuminate at least one particle and to capture and/or process the scattered light signal history used to determine values of the particle properties. The apparatus utilizes a one component light beam A consisting of a single color and single polarization, generated by a laser 12 that is intensity attenuated by means of a neutral density filter 14 and split into two beams 1 and 2 by a beamsplitter 16. Beam 1 passes through a Bragg cell 20 which frequency shifts the beam by $F_0$, where $F_0$ is typically 40 MHz. Beam 2 is reflected by a reflector 18 through a Bragg cell 21 wherein it is frequency shifted by $F_0+\Delta F$, where $|\Delta F| \geq 1$ KHz in typical applications. Beam 2 is then redirected by reflector 22 through lens 23 and polarizer 24, to insure purity of the single beam component. From the polarizer beam 2 is directed by reflector 26 through the window 26A and through the center of sample chamber 40 containing at least one particle a liquid or gas suspension fluid to a light trap 32. In a like manner, beam 1 is reflected off reflector 28 and directed through lens 29 and polarizer 30, to insure purity of the single beam component. Beam 1 is then directed by reflector 31 through the window 31A to intersect beam 2 at the center of the sample chamber 40. A light trap 34 is positioned to trap beam 1 at the far side of the sample chamber. The beams intersect at angle $\Psi$ which is bisected by an axis Z. Perpendicular to axis Z is an X labelled axis. A lens 36 is positioned with its center on the Z axis to focus forward scattered light from at least one particle within the intersection volume of beams 1 and 2 onto photomultiplier tube (PMT) 42. A polarizer 37 typically passing light having the polarization angle of the original beams A, 1, and 2, is inserted in the beam path to insure purity of the light component detected. A mask 38 is interposed in the beam path centered on the Z axis to remove defocused light. The lens 36 and the PMT 42 are also centered on axis Z. Signal storage and processing equipment 43 receives, as an input, the electrical signals from PMT 42 and performs storage of the signal history and signal processing methodologies on the received signals by signal processing equipment 43 and 60 to provide output data $S_0(t)$ and $S(t)$ relating to the characteristics of the particle illuminated in the intersection volume contained at the center of chamber 40.

Consider a plane-wave element in each of two laser beams whose axes lie in the x-z plane and intersect with angle $\Psi$ at the origin of the x-z coordinate system, as shown in FIG. 1A. The electric field vectors of these two beam elements are $$\underline{E}_1(\underline{r},t) = \underline{n}_1 E_{10} e^{i(\omega_1 t - \underline{k}_1 \cdot \underline{r})} \quad \text{(A1a)}$$

$$\underline{E}_2(\underline{r},t) = \underline{n}_2 E_{20} e^{i(\omega_2 t - \underline{k}_2 \cdot \underline{r})} \quad \text{(A1b)}$$

where the unit vectors $\underline{n}_1$ and $\underline{n}_2$ specify the direction of polarization of beams 1 and 2, $E_{10}$ and $E_{20}$ the amplitudes, $\omega_1$ and $\omega_2$ the angular frequencies, $\underline{k}_1$ and $\underline{k}_2$ the wave vectors having magnitudes $k_1 = \omega_1/c$ and $k_2 = \omega_2/c$ with $c$ the speed of light in the medium. The unit vectors $\underline{\kappa}_1 = \underline{k}_1/k_1$ and $\underline{\kappa}_2 = \underline{k}_2/k_2$ define the directions of propagation of the two beam elements in the medium and the radius vector is given by $\underline{r} = x\underline{x} + z\underline{z}$ with $\underline{x}$ and $\underline{z}$ the unit vectors in the x and z axis directions. Since $c = \omega\lambda/(2\pi)$, where $\lambda$ is the wavelength in the medium, we can also write for the magnitude of the wave vectors $k_1 = 2\pi/\lambda_1$ and $k_2 = 2\pi/\lambda_2$.

When both beams are polarized in the same direction ($\underline{n}_1 = \underline{n}_2$) the fields (A1) of the two elements are summed as scalers within the intersection volume. Thus, within the intersection volume $$E(x,z,t) = E_1(x,z,t) + E_2(x,z,t) = E_{10} e^{i[\omega_1 t + k_1 \sin(\Psi/2)x - k_1 \cos(\Psi/2)z]} + E_{20} e^{i[\omega_2 t - k_2 \sin(\Psi/2)x - k_2 \cos(\Psi/2)z]} \quad \text{(A2)}$$

where we have used $$\underline{k}_1 \cdot \underline{r} = -k_1 \sin(\Psi/2)x + k_1 \cos(\Psi/2)z$$

$$\underline{k}_2 \cdot \underline{r} = k_2 \sin(\Psi/2)x + k_2 \cos(\Psi/2)z.$$

Now define $\omega = \omega_1 + \Delta\omega/2 = \omega_2 - \Delta\omega/2$ with $\Delta\omega = \omega_2 - \omega_1$ and $k = k_1 + \Delta k/2 = k_2 - \Delta k/2$ with $\Delta k = k_2 - k_1$. We also define $\Delta E_0 = E_{20} - E_{10}$. It follows that $$E(x, z, t) = (\Delta E_0/E_{20})E_2(x, z, t) + 2E_{10}\cos[\Delta\omega t/2 - k\sin(\psi/2)x] \quad \text{(A3)}$$

$$* e^{i[\omega t - (\Delta k/2)\sin(\psi/2)x - (k + \Delta k/2)\cos(\psi/2)z]}.$$

Thus, in the intersection volume the electric field is the sum of a plane wave field of amplitude $\Delta E_0$ and a fringe pattern field of amplitude $2E_{10}\cos[\Delta\omega t/2 - k\sin(\Psi/2)x]$.

The direction of propagation $\underline{\kappa} = \kappa_x \underline{x} + \kappa_z \underline{z}$ of the fringe field light is determined from the second term of (A3) with $$\begin{aligned} \underline{k} \cdot \underline{r} &= k\underline{\kappa} \cdot (x\underline{x} + z\underline{z}) \\ &= (\Delta k/2)\sin(\psi/2)x + (k + \Delta k/2)\cos(\psi/2)z \end{aligned}$$

from which $\kappa_x = [\Delta k/(2k)]\sin(\Psi/2)$ and $\kappa_z = [1 + \Delta k/(2k)]\cos(\Psi/2)$. The ratio $\kappa_x/\kappa_z$ provides the tangent of the angle $\Psi'$ between $\underline{\kappa}$ and the z axis.

$$\tan \Psi' = [\Delta k/(2k + \Delta k)] \tan (\Psi/2).$$

For MDLS systems in general, $k$ exceeds $\Delta k$ by 8 to 10 orders of magnitude so that any finite aperture centered on the z axis will pass essentially forward scattered light from the fringe field. However, light from the plane wave field of amplitude $\Delta E_0$, the first term of equation (A3), will not be forward scattered through the same aperture. To obtain only forward scattered light the two beam elements must be matched in their amplitudes so that $\Delta E_0 = 0$.

The local intensity of the light is given by $$J(x,z,t) = (\epsilon c/2) \langle E(x,z,t) E^*(x,z,t) \rangle \quad \text{(A4)}$$

where $\epsilon$ is here the dielectric constant of the medium, $E(x,z,t)$ the local electric field strength and $E^*(x,z,t)$ its conjugate. The angular brackets indicate the time average over an interval long compared to the period of the field (~1 fsec) but short compared to, say, the resolution interval of the detector (~1 nsec). Thus, noting the J is independent of z in the intersection volume, $$J(x,t) = (\epsilon c/2)\{(E_{20} - E_{10})^2 + 2E_{10}E_{20}[1 + \cos(\Delta \omega t - Kx)]\} \quad \text{(A5a)}$$

where $K = (4\pi/\lambda)\sin(\Psi/2)$. In terms of the intensities $I_1$ and $I_2$ of the two beam elements, $$J(x,t) = I_1 + I_2 + 2(I_1 I_2)^{5.0} \cos (\Delta\omega t - Kx) \quad \text{(A5b)}$$

from which equation (2) is obtained. When $I_1 = I_2$, $$J(x,t) = 2I_1[1 + \cos (\Delta\omega t - Kx)]. \quad \text{(A5c)}$$

The separation of fringe planes $\delta$ is derived from the periodicity requirement $K(x+\delta) - Kx = K\delta = 2\pi$ which gives $\delta = 2\pi/K$.

The velocity with which the intensity distribution of the fringe field translates in the x-direction is determined from the expression relating time and position of any feature of the field, namely, $\Delta\omega t - Kx = $ constant. Upon taking the time derivative of this expression we obtain $V_f = \Delta\omega/K$.

Figure 1B:
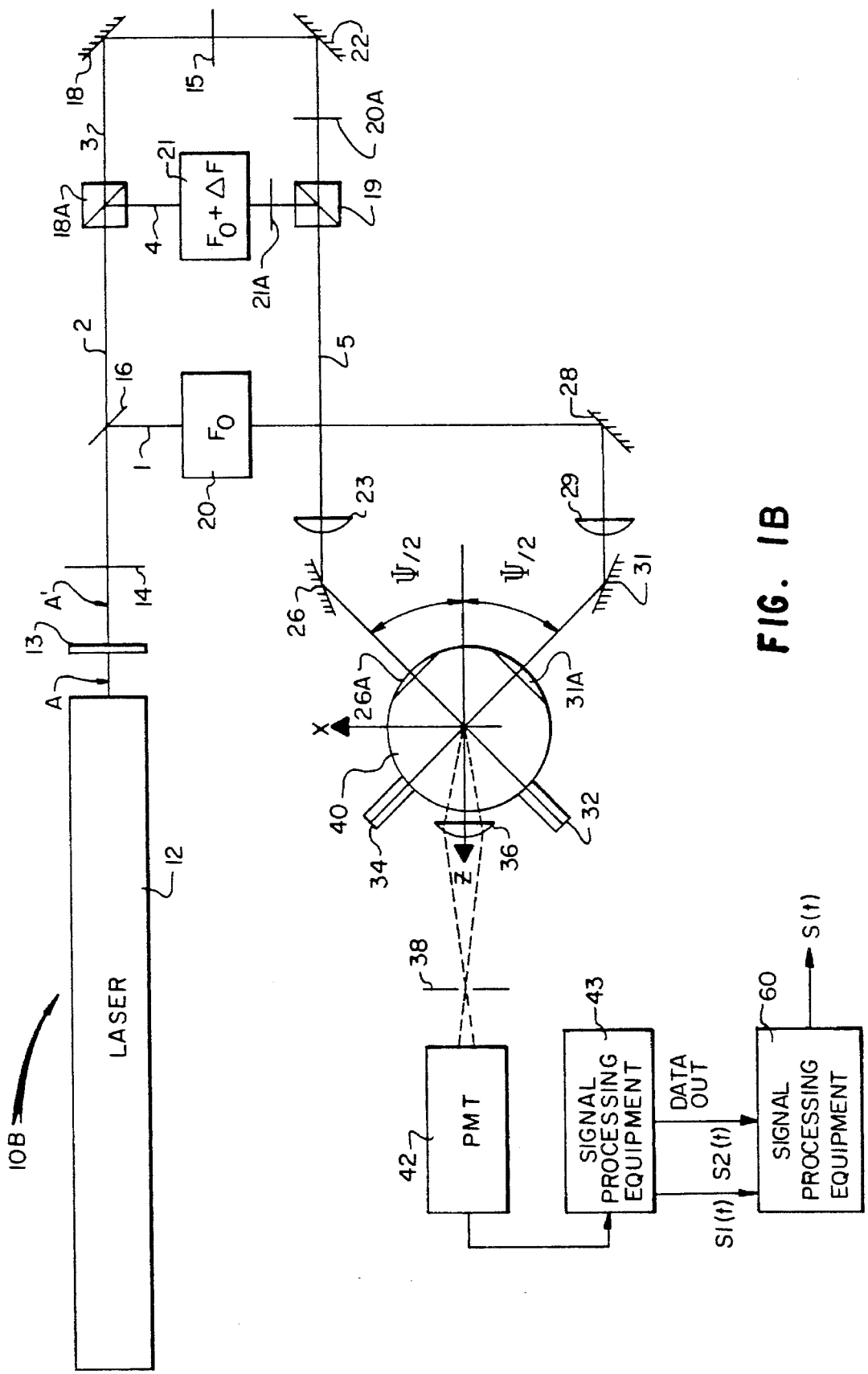
FIG. 1B is a block diagram of an MDLS device for illuminating a particle with light having two components (polarization and/or color) each of which has a fringe pattern intensity field that is independently modulated to give two independent time and displacement periodicities. Also shown are associated signal detection and processing equipment.

FIG. 1B illustrates an MDLS device 10B which is used to illuminate at least one particle with light containing two components in each of two beams that are combined in the intersection volume at the center of chamber 40 to form the independently modulated fringe patterns, one from each component. Light beam A from laser 12 passes through a half-wave plate 13 which can be rotated to fix the direction of polarization of light in beam A' in order to divide substantially equally the light in beams 3 and 4. Light in beam A' is intensity attenuated by neutral density filter 14 and split into beams 1 and 2 by beamsplitter 16. Both beams 1 and 2 contain two components, namely, light having vertical and horizontal polarization. Beam 1, containing substantially half the power of beam A', is directed by beamsplitter 16 through a Bragg cell 20 which frequency shifts by $F_0$ both components of beam 1. After passing through Bragg cell 20 beam 1 is directed by reflector 28 through lens 29 (optional) and onto reflector 31 which directs beam 1 through window 31A into the center of sample chamber 40. Beam 1 then passes through the center of chamber 40 and is trapped in a light trap 34 at the far side of chamber 40. Beam 2 is separated into the two beams 3 and 4 each having only one component (polarization) by polarizing beamsplitter 18A. Beam 3 containing the horizontally polarized component of beam 2 is directed by reflector 18 through a neutral density filter 15 (optional) used to adjust the intensity balance between beams 3 and 4 upon their recombination as beam 5 and to reflector 22 and to polarizer 20A (optional) to insure purity of the horizontally polarized light component of beam 3. Beam 4 containing the vertically polarized light component of beam 2 is directed by polarizing beamsplitter 18A through Bragg cell 21 which frequency shifts the beam $F_0 + \Delta F$. Beam 4 next passes through polarizer 21A to insure purity of the vertically polarized light component of beam 4. Beam 3 and beam 4 are recombined into beam 5 by polarizing beamsplitter 19 such that beam 5 contains two components of substantially equal intensity, namely, the horizontally polarized light component of beam 3 that is not frequency shifted and the vertically polarized light component of beam 4 that is frequency shifted by $F_0 + \Delta F$. Beam 5 is next passed through lens 23 (optional) and onto reflector 26 which directs beam 5 through window 26A through the center of sample chamber 40 and into light trap 32. Beams 1 and 5 intersect at the center of chamber 40 with intersection angle $\Psi$ which is bisected by an axis Z. Perpendicular to axis Z is an axis labelled X. A lens 36 is positioned on the Z axis to focus scattered light from any particle in the intersection volume of beams 1 and 5 onto photomultiplier tube (PMT) 42. Mask 38 is positioned intermediate between the lens 36 and the PMT 42 to prevent undesired stray light from reaching PMT 42. Electronic and signal processing equipment 43 receives, as an input, the electrical signals from PMT 42 and performs electronic filtering, signal storage and signal processing methodologies on the signal received from PMT 42. The signal from PMT 42 contains one signal component due to the horizontally polarized light components of beams 1 and 5 and therefore contains this signal component at the modulation or bias frequency $F_0$. The signal from PMT 42 will also contain a second signal component due to the vertically polarized light components of beams 1 and 5 and will therefore contain this signal component at the modulation or bias frequency $F_0+\Delta F-F_0=\Delta F$. Since $\Delta F \ll F_0$ scattered light signals corresponding to these two signal components can be electronically separated to provide two isolated signal components. This isolation is useful since the high frequency signal component is proportional to the instantaneous value of the product of the mean illumination intensity over many of the high frequency periods and the instantaneous light scattering cross-section of the particle, the latter quantity being particle orientation dependent. The low frequency signal component is proportional to the product of the instantaneous illumination intensity and the light scattering cross-section of the particle, the former quantity being particle displacement dependent while the latter is particle orientation dependent. The ratio of the low frequency signal component and the high frequency signal component thus provides a signal that depends only on particle location and is independent of particle orientation. Output data relating to location dependent properties of the particle such as the translational friction coefficient of the particle in the suspending fluid and the particle mass can be extracted directly from this ratio of low and high frequency signal components provided by signal processing equipment 60 without extensive and complex analysis. Likewise, output data relating to orientation dependent properties of the particle can be extracted directly from the high frequency signal component.

Figure 1C:
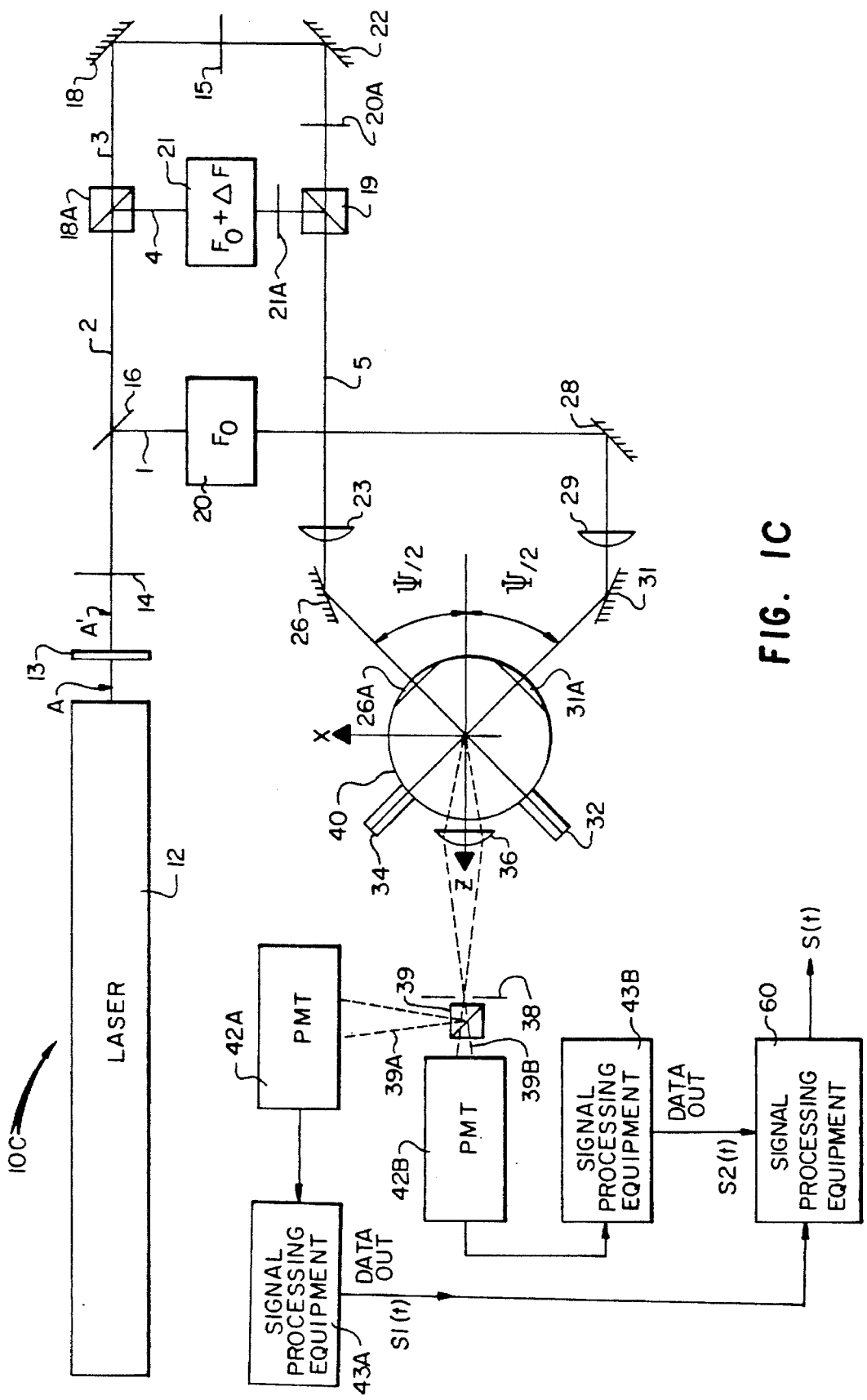
FIG. 1C is a block diagram of an MDLS device similar to that of FIG. 1B but utilizing different optical, electronic and signal processing equipment.

In FIG. 1C an apparatus 10C similar in function to that of FIG. 1B is illustrated. The apparatus of FIG. 1C is identical to that of FIG. 1B in its components and their functions with the exception of components 39, 42A, 42B, 43A, 43B and output signals S1(t) and S2(t), which components and their functions are here described. Alternatively to the electronic separation of the high and low frequency components of the scattered light signal utilized in the apparatus of FIG. 1B, the apparatus of FIG. 1C separates these two signal components optically by use of a polarizing beamsplitter 39. Scattered light signal containing the two components (polarizations) and passing through mask 38 of FIG. 1C is separated into two beams 39A and 39B which substantially contain, respectively, the horizontally and vertically polarized light scattered from the particle in the intersection volume at the center of sample chamber 40. One component of this scattered light signal, the horizontally polarized component beam 39A which is the component modulated at high frequency $F_0$, is detected by PMT 42A which provides in response an electrical output signal captured or processed by signal processing equipment 43A to provide data output signal S1(t). Signal processing equipment includes means for providing the time averaged mean signal over an interval which is long compared to the period $1/F_0$ but short compared to the much longer period $1/\Delta F$. Thus, the electrical signal S1(t) is proportional to the product of the local time averaged intensity and the instantaneous value of the light scattering cross-section of the particle which cross-section may vary substantially over time intervals $\gg 1/F_0$ due to random Brownian rotations of the particle. The second component of the scattered light signal from the particle in the intersection volume at the center of chamber 40, the vertically polarized component beam 39B which is the component modulated at the much lower frequency $\Delta F$, is detected by PMT 42B which provides an electrical output signal captured or processed by signal processing equipment 43B to provide data output signal S2(t). Thus, output signal S2(t) is proportional to the product of the light scattering cross-section of the particle and the instantaneous illumination intensity which depends on the instantaneous particle displacement in the x-direction. The ratio S2(t)/S1(t) at time t obtained by use of signal processing equipment 60 depends only on particle displacement x at time t.

Figure 2A:
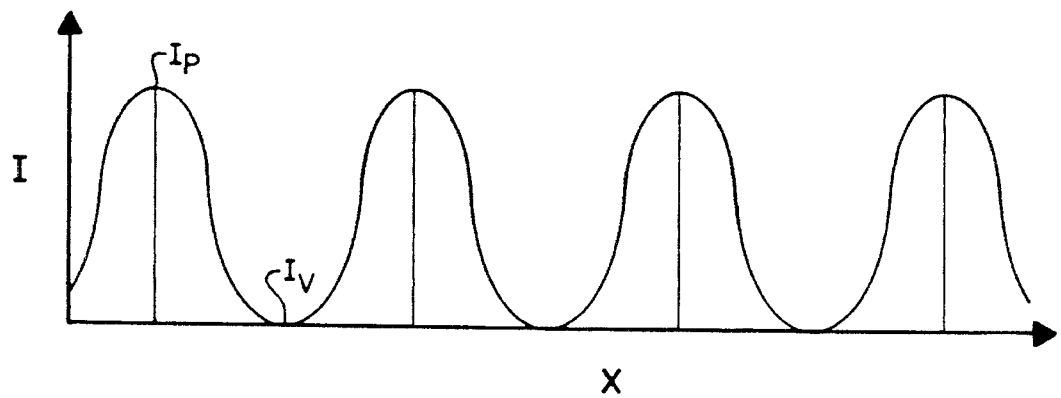
FIG. 2A is a waveform illustrating the illumination intensity pattern caused by destructive interference of one component of light within the intersection volume of the two crossed beams shown in FIGS. 1A, 1B and 1C at one instant in time.
Figure 2B:
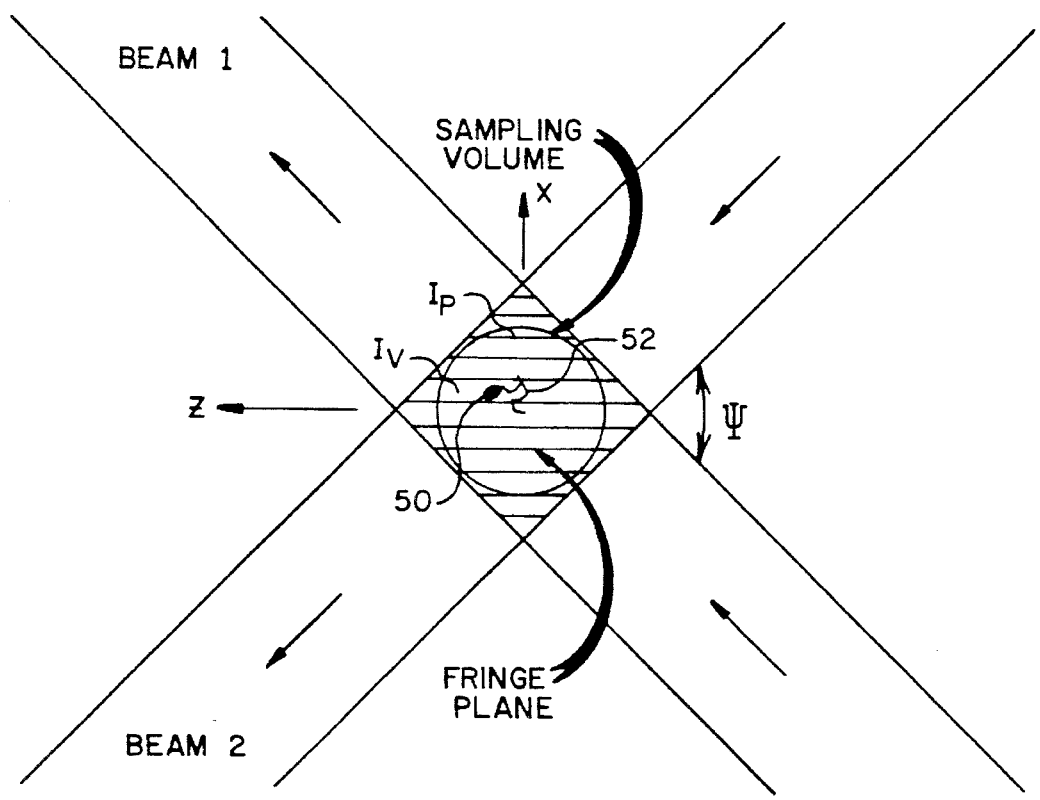
FIG. 2B is a rendering of the fringe pattern formed at one instant in time within the intersection volume by the destructive interference of one component of light in the two beams of FIGS. 1A, 1B and 1C.

FIG. 2A illustrates in a cross-sectional view the local intensity of one component (polarization) versus x-direction displacement within the intersection volume of the two beams at the center of chamber 40 at one instant in time. The amplitude I is shown varying between a maximum value of $I_p$ and a minimum value of $I_v$. This interference fringe pattern (intensity distribution) is moving in the x-direction with the constant velocity $V_f=\Delta\omega/K$ with $\Delta\omega$ the angular bias frequency $(=2\pi\Delta F$ or $2\pi F_0)$ and K is the magnitude of the scattering vector $=4\pi n_f/\lambda_0 \sin(\Psi/2)$ where $n_f$ is the index of the fluid medium and $\lambda_0$ the wavelength of the laser light in vacuum. Referring to FIG. 2B, the intersection of beams 1 and 2 in FIG. 1A establishes one interference fringe pattern or beams 1 and 5 in FIGS. 1B and 1C establishes two superimposed interference fringe patterns of alternate, parallel planes of high intensity $I_p$ separated by planes of low intensity $I_v$ throughout the central portion of the intersection volume. When the MDLS device contains light beams having two components, two such intensity fields are superimposed since, for example, light having a horizontal electric field vector (polarization) does not interfere with light having a vertical electric field vector (polarization). Thus the two superimposed fringe patterns move across the intersection volume each at its own characteristic velocity $(=2\pi\Delta F/K$ and $2\pi F_0/K)$ without interfering with each other.

For the light component having polarization direction in the plane of FIGS. 1A, 1B or 1C (horizontal polarization), the polarization vectors of the two beams are not aligned because the beams are inclined by angle $\Psi$. In this case the intensity field fringe pattern has a larger value of the minimum intensity $I_v$ while the maximum intensity $I_p$ may be unchanged.

A high frequency pass filter receiving the electrical signal from the detector (PMT) 42 removes the signal component due to the background illumination intensity $I_v$ passing only the fluctuating signal component. For light having polarization vector normal to the plane of FIGS. 1A, 1B and 1C (vertical polarization), the polarization vectors are always aligned and the background illumination intensity, $I_v$, is small. Vertical polarization thus gives the largest intensity modulation.

A particle 50 moves, for example, by random Brownian translations over an example trajectory 52. The illumination intensity of the particle 50 is time and displacement modulated according to Equation (A5b), $$J(x,t)=I_0[1+v \cos(\Delta\omega t-Kx)] \qquad (2)$$

where $I_0=I_1+I_2$ is the local mean intensity, $v=2\rho^{1/2}/(1+\rho)$ [with $\rho=I_1/I_2$] the local fringe pattern visibility or relative amplitude of the fluctuating intensity, $\Delta\omega=2\pi\Delta F$ is the angular bias frequency, $K=(4\pi/\lambda)\sin(\Psi/2)$ is the magnitude of the scattering vector, $\Psi$ the intersection angle of the two beams of FIGS. 1A, 1B and 1C and $\lambda$ the wavelength of the light in the suspension fluid in beams 1 and 2 of FIG. 1A or of beams 1 and 5 of FIGS. 1B and 1C (equal to adequate precision) and where x is the displacement normal to the fringe planes as indicated in FIGS. 1A, 1B, 1C, 2A and 2B. The visibility v obtains its maximum value of unity when $\rho=1$, but the maximum is flat and broad with $v \geq 0.98$ when $0.667<\rho<1.50$.

To measure individual particles, particles are introduced into the sample chamber 40 at sufficiently low concentration so that a particle is located in the intersection volume no more than 10 percent of the time. Only rarely then will more than one particle occupy the intersection volume, resulting in negligible coincidence errors. To measure more than one particle at a time, particles are introduced at much higher concentration so that many are simultaneously in the intersection volume. In this case the properties measured are weighted mean values.

While a particle resides in the intersection volume of the device shown in FIG. 1A it scatters light through lens 36, analyzer 37 and mask 38 onto detector (PMT) 42. Typically for MDLS device 10A, only scattered light have the same polarization as the incident light is detected. As illustrated in FIG. 1A, this light is scattered within a small solid angle centered on the forward direction. Non-forward scattered light can also be observed by movement of the detector-mask analyzer-lens axis off the central axis Z.

When the PMT signal indicates the presence of a particle in the intersection volume (exceeds a threshold value), the signal is captured, stored or processed. For example, a digital correlator can be used to accumulate the correlation function of the PMT (scattered light) signal until the particle leaves the intersection volume the (PMT signal falls below the threshold value). The measured autocorrelation function for each particle is stored and processed later or processed on-line to extract the property values of interest from which precise distributions can be determined. Example computer programs for extraction of some property values are given in Appendices B, C and D.

To infer the property values from the captured or processed data, a suitable model that relates the data and the particle properties is required. We illustrate here the basis of such models and outline example analysis and signal processing methods.

For a particle 50 suspended in a fluid at absolute temperature T, the probability that it will displace in the x-direction the net length $\Delta x$ by random Brownian displacements in time interval t is given by the so-called transition probability expression $$p(\Delta x,t)=(2\pi\sigma^2)^{-1/2} \exp[-\Delta x^2/(2\sigma^2)] \quad (3)$$

where $\sigma^2$ is the mean-square-x-displacement of the particle in time interval t given by $$\sigma^2=2kT/(m\beta^2)[\beta t-1+\exp(-\beta t)]=2DtF(\beta t) \quad (4)$$

where $F(\zeta)=1-[1-\exp(-\zeta)]/\zeta$, k is Boltzmann's constant, m the mass of the particle 50, $\beta=f/m$, f the translational friction coefficient of the particle in the fluid and $D=kT/f$. Values of the function $F(\zeta)$ versus $\zeta$ are given in Table 1. Note that the large $\zeta$ asymptotic expression, $F(\zeta)=1-1/\zeta$, is substantially correct for $\zeta \geq 3$, a result that will be utilized below.

TABLE 1

| $\zeta$ | $F(\zeta)$ | $\zeta$ | $F(\zeta)$ | $\zeta$ | $F(\zeta)$ |
| --- | --- | --- | --- | --- | --- |
| $\to \infty$ | $1-1/\zeta$ | 10.0 | 0.9000 | 0.8 | 0.3117 |
| 100.0 | 0.9900 | 8.0 | 0.8750 | 0.6 | 0.2480 |

TABLE 1-continued

| $\zeta$ | $F(\zeta)$ | $\zeta$ | $F(\zeta)$ | $\zeta$ | $F(\zeta)$ |
| --- | --- | --- | --- | --- | --- |
| 80.0 | 0.9875 | 6.0 | 0.8337 | 0.4 | 0.1758 |
| 60.0 | 0.9833 | 4.0 | 0.7546 | 0.3 | 0.1361 |
| 40.0 | 0.9750 | 3.0 | 0.6833 | 0.2 | 0.09365 |
| 30.0 | 0.9667 | 2.0 | 0.5677 | 0.1 | 0.04837 |
| 20.0 | 0.9500 | 1.0 | 0.3679 | $\to 0$ | $\zeta/2$ |

When the suspending fluid is a liquid or a gas at normal temperature and pressure, $\zeta=\beta t \gg 1$ for values of t of current interest so that, to adequate accuracy, $F(\zeta)=1$, $\sigma^2=2Dt$ and determination of $\sigma^2$ at one or more values of t provides only the value of $D=kT/f$ and information about the particle that derives therefrom. For cases in which $\zeta=\beta t \leq 100$, such as when the fluid is a gas at reduced pressure, the value of particle mass or particle mass and friction coefficient may be determined. For example, when $0.1 \leq \zeta \leq 20$, then $F(\zeta)<1$ for time intervals of current interest and $\sigma^2=2DtF(\zeta)$ and determination of $\sigma^2$ at two or more values of t provides both $D=kT/f$ and $\beta=f/m$ and information that derives therefrom. As another example, when a suspending gas has pressure sufficiently small so that $\zeta=\beta t \leq 0.1$ for time intervals of current interest, $\sigma^2=kTt^2/m$ so that determination of at least one $\sigma^2$ and t data pair provides the particle mass $m=kTt^2/\sigma^2$. Thus, measurement of $\sigma^2$ and t data pairs with at least one pair in the range of $0.1<\zeta<100$ may allow determination of at least two properties of the particle.

Consider, as a first example, particle 50 located near the center of chamber 40 within the intersection volume of beams 1 and 5 of FIGS. 1B or 1C which causes the particle to be illuminated by two superimposed modulated intensity fields both characterized by equations having the form of Equation (2). The signal $S(t)=S2(t)/S1(t)$ obtained from signal processing equipment 60 is coupled so that only the a.c. component of signal $S(t)$ is passed into a sensor circuit of equipment 60. When the particle 50 observed in MDLS device 10A either has an orientation dependence of its scattering cross-section that is zero or relatively weak or is constrained to remain in a fixed orientation, such as by use of an imposed electrostatic or aerodynamic field, then output signal $S_0(t)$ of device 10A is functionally equivalent to $S(t)$ and the methods utilized to extract property values and other information from $S(t)$ can also be used to extract property values and other information from $S_0(t)$. Accordingly, the output signal $S_0(t)$ from the apparatus of FIG. 1A can be coupled into a sensor circuit of equipment 60 and the following description then applies equally to the output of equipment 60 from apparatus 10A, 10B and 10C.

Figure 4:
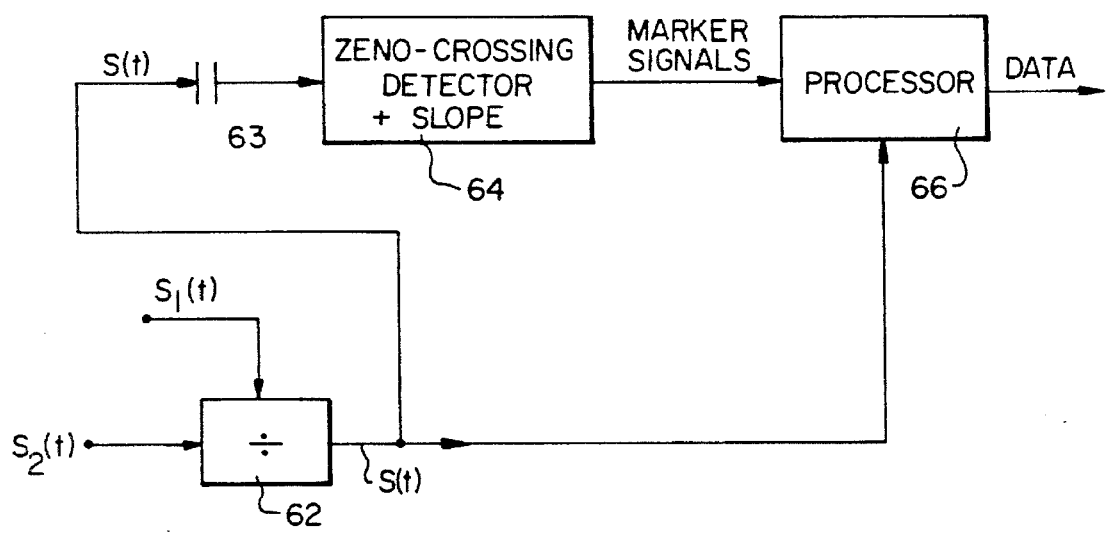
FIG. 4 is a block diagram of electronic and signal processing equipment that may be used to capture and/or process the scattered light signal history of a particle in the device of FIGS. 1A, 1B or 1C.

In FIG. 4 are illustrated some of the components of signal processing equipment 60. Referring to FIG. 4, the signals $S1(t)$ and $S2(t)$ are applied to a divider 62. The output from the divider is the signal $S(t)=S2(t)/S1(t)$ which is applied to the input of a zero-crossing detector for positive slope crossings 64 via a d.c. decoupler such as capacitor 63. The marker signals generated by detector 64 are transmitted to a processor 66 which determines the time intervals between selected marker signals (nearest neighbor, second nearest neighbors, ...) and provides the sequence of these interval values as digitized quantities on the output data line of processor 66.

The sensor circuit detects when the a.c. component of $S(t)$ crosses the zero level with positive slope and generates an electrical marker signal at each such crossing. These marker signals thus occur at the time values at which the a.c. component of the illumination intensity given by Equation (2) is zero with positive slope. Thus, for time interval $\Delta t$ between two selected marker signals and particle displacement $\Delta x$ during the interval, it follows from Equation (2) that $$O=\cos[\Delta\omega(t_0+\Delta t)-K(x_0+\Delta x)].$$

Defining the initial time $t_0$ and location $x_0$ to give a reference condition at which the a.c. component of the illumination intensity crosses zero with positive slope, namely, $\Delta\omega t_0 - Kx_0 = 3\pi/2$, at which instant the first marker signal occurs, we obtain for the condition for subsequent marker signals $$\Delta\omega\Delta t - K\Delta x = 2m_0\pi,$$

where $m_0 = 1, 2, 3, 4, \ldots$

For nearest neighbor marker signals $m_0 = 1$. For second nearest neighbor marker signals $m_0 = 2$. For the $\eta$th nearest neighbor marker signals $m_0 = \eta$. It follows that $\Delta x$ and $\Delta t$ must be related by the expression $$\Delta x = [\Delta\omega\Delta t - 2m_0\pi]-K. \qquad (5)$$

When a large number, n, of time intervals $\Delta t$ is measured for a particle 50 in the modulated illumination intensity field and when the number of measurements, $n_i$, for which $\Delta t = \Delta t_1$ is determined, by signal processing equipment 60, the probability of observing $\Delta t = \Delta t_i$ and $\Delta x = \Delta x_i$ is given by the ratio $P_i = n_i/n$. This probability must correspond to that given, for example, by the transition probability expression (3) so that $$P_i = n_i/n = (2\pi\sigma^2)^{-1/2} \exp[-\Delta x_i^2/(2\sigma^2)]Sx_i \qquad (6)$$

where $Sx_i$ is the resolution or channel width of the displacement $\Delta x_i$.

A time series analysis of the signal $S(t)$ to obtain at least one property of particle 50 can be performed as follows. The sequence of n measured time intervals $\Delta t$ between marker signals is used with Equation (5) to obtain the corresponding displacements $\Delta x$. The number of intervals $n_i$ having specified time interval $\Delta t_i$ and displacement $\Delta x_i$ is determined from this sequence and the ratio $p_i = n_i/n$ is determined for each of several values of $\Delta t_i$. These ratios are used with the corresponding values of $\Delta x_i$ and, for example, Equation (6) to determine $\sigma^2$ for each of the several $\Delta t_i$ time interval values. The values of $\sigma^2$ at each of these $\Delta t$ time interval values are used with, for example, $$\sigma^2 = 2D\Delta t F(\beta\Delta t) \qquad (7)$$

to determine $D = kT/f$, $D$ and $\beta = f/m$ or m in the cases where the $\Delta t$ data correspond to $\beta\Delta t \gg 1$, $0.1 < \beta\Delta t < 100$ or $\beta\Delta t \leq 0.1$, respectively.

A time series analysis methodology like the one illustrated above will be adequate when the noise contained in the signal $S(t)$ is relatively low, as occurs for large particles with large light scattering cross-sections. For particles having light scattering cross-sections which are relatively small, other methods are preferred which employ, for example, one or more signal processing techniques which allow clean extraction of signals buried deeply in noise.

Figure 5:
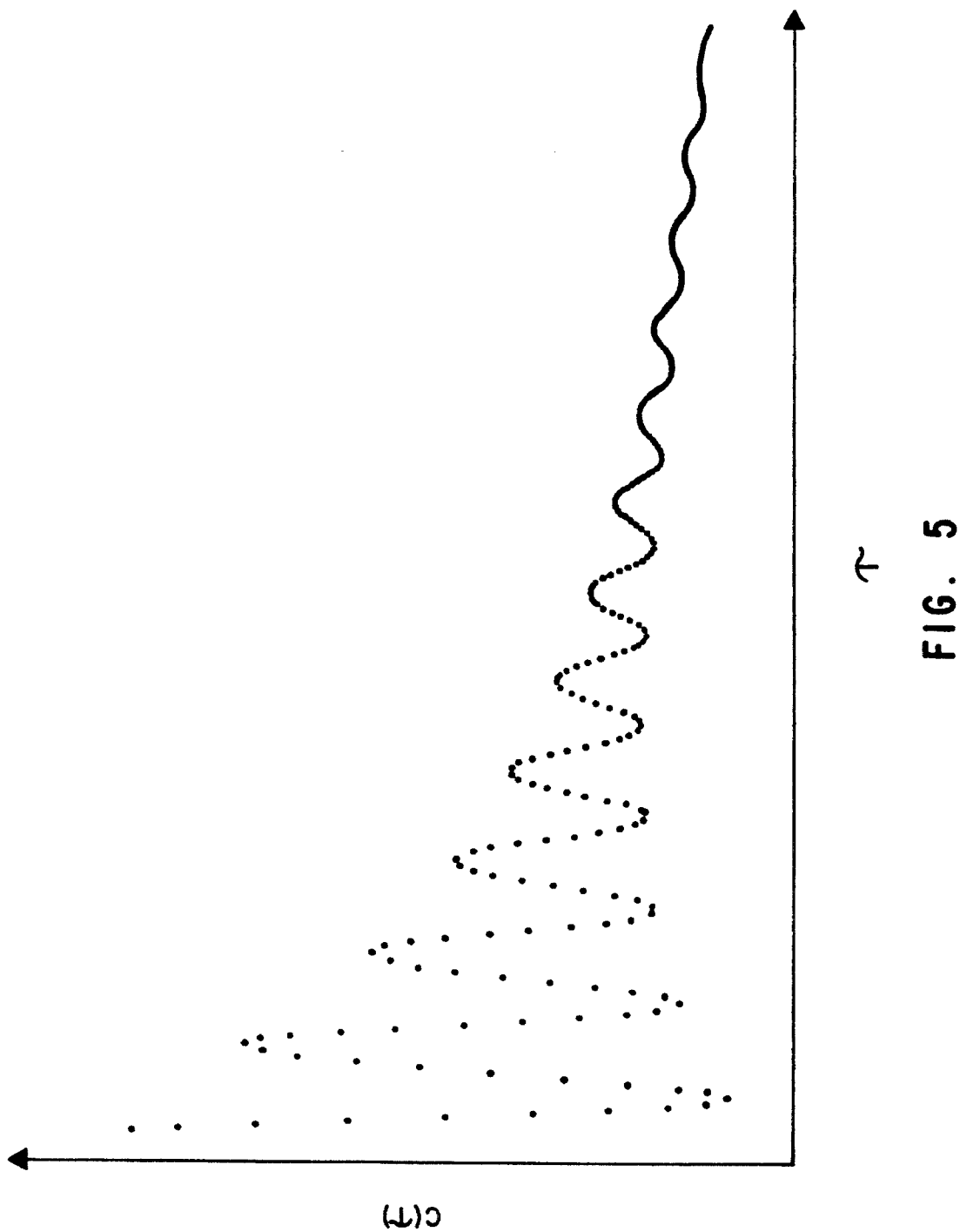
FIG. 5 is a point plot of a measured correlation function for a sample particle made in accordance with one method of the present invention.

Now consider, as a second example, the determination of at least one property of a particle 50 in chamber 40 by use of the autocorrelation function of the signal $S(t)$ obtained using device 10B or 10C or signal $S_0(t)$ obtained using device 10A subject to the conditions previously stated. An example of such an autocorrelation function as measured with device 10A is shown in FIG. 5. The same methods can be used to determine at least one property of the particle 50 in chamber 40 by use of the autocorrelation function of the signal $S(t)$ obtained using the device 10D of FIG. 6 which device will be described hereinafter. The autocorrelation function (or simply correlation function hereafter) is formed by use of a correlator, to which the signal $S(t)$ is transmitted. It remains, however, to show how the correlation function depends on the properties of particle 50 and, therefore, how the correlation function can be used to obtain at least one property of particle 50.

For example, in the modulated illumination device 10C of FIG. 1C, the signal $S(t) = S2(t)/S1(t)$ depends on $I(t) = J(x_p(t), t)$ according to Equation (2) where $x_p(t)$ is the instantaneous particle x-location and on a multiplicative instrument constant $\alpha$ $$S(t) = \alpha I_n(t) \qquad (9)$$

where $I_n(t) = I(t)/I_0$ with $I_0$ the instantaneous (short compared to $1/\Delta F$ but long compared to $1/F_0$) time averaged intensity of illumination on particle 50 obtained, within a multiplicative constant, from the (short) time average of signal $S1(t)$ of the device 10C. It is useful to express $I_n(t)$ in the form $$I_n(t) = 1 + \gamma(t) \qquad (10)$$

where $\gamma(t)$ is the relative fluctuation of $I_n(t)$ at time t. The correlation function of $S(t)$ is defined by $$C(\tau) = \langle S(t)S(t+\tau)\rangle \qquad (11)$$

where $\tau$ is the delay time and where the angular brackets denote the time averaged value. Substitution of Equations (9) and (10) into Equation (11) gives $$C(\tau) = \alpha^2 \langle [1+\gamma(t)][1+\gamma(t+\tau)]\rangle$$

or, as is readily shown, $$C(\tau) = \alpha^2 [1 + \langle \gamma(t)\gamma(t+\tau)\rangle]. \qquad (12)$$

To determine $C(\tau)$ it remains only to determine $\langle \gamma(t)\gamma(t+\tau)\rangle$. This time average is readily determined by calculating the ensemble average in place of the time average, since the two are equivalent.

To calculate the ensemble average we first note that the angular bias frequency $\Delta\omega$ of Equation (2) can be expressed in terms of the fringe field velocity $V_f$ $$\Delta\omega = 2\pi V_f/\delta$$

where $\delta = 2\pi/K$ is the separation of the fringe planes (Appendix A). For the example case when particle 50 moves with constant average velocity $V_p$, such as by sedimentation or convection in a moving suspending fluid, and by random Brownian translations, particle location is given by $$x_p(t) = x_0 + V_p t + \Delta x(t) \qquad (13)$$

where $x_0$ is the initial particle location and $\Delta x(t)$ is the net x-direction displacement of the particle in time interval t due to the random Brownian translations. The relative fluctuation in illumination intensity incident on the particle is therefore, from the a.c. component of Equations (2) and (13), equal to $$\gamma(t) = v\cos[\omega t - \phi(t)] \qquad (14)$$

where $\omega = 2\pi(V_f - V_p)/\delta$ and $\phi(t) = Kx$ with $x = x_0 + \Delta x(t)$, the apparent initial location of the particle at time t.

The correlation function is thus given by the ensemble average $$C(\tau)/\alpha^2 - 1 = \lim_{L\to\infty} v^2/(2L) \int_{-L}^{L} dx_0 \int_{-\infty}^{\infty} dx \quad (15)$$

$$C(\tau)/\alpha^2 - 1 = \lim_{L\to\infty} v^2/(2L) \int_{-L}^{L} dx_0 \int_{-\infty}^{\infty} dx$$

$$p(x, \tau; x_0)\cos(Kx_0)\cos(\omega\tau - Kx)$$

where $p(x,\tau;x_0)$ is the transition probability, i.e., the probability density that a particle is located at x at time $\tau$ when it began at location $x_0$ at time zero. For a particle undergoing pure Brownian motion, for example, $$p(x,\tau;x_0)=(2\pi\sigma^2)^{-1/2} \exp[-\Delta x^2/(2\sigma^2)] \quad (16)$$

where, as above, $\sigma^2=2D\tau F(\zeta)$, $\zeta=\beta\tau=f\tau/m$ and $F(\zeta)=1-[1-\exp(-\zeta)]-\zeta$ with values of $F(\zeta)$ for selected values of $\zeta$ given in Table 1. Evaluation of the integrals (15) gives the desired correlation function $$C(\tau)=\alpha^2[1+v^2/2 \exp(-K^2\sigma^2/2) \cos(\omega\tau)]. \quad (17)$$

Determination of $C(\tau)$ by use of a correlator together with the analytical expression (17) allows extraction of $\sigma^2$ at each of several values of delay time $\tau$ by suitable data analysis methods, such as least-squares fitting of Equation (17) to the measured $C(\tau)$. These $\sigma^2$ are $\tau$ data pairs for the particle 50 together with the expressions $\sigma^2=2D\tau F(\beta\tau)$ and $F(\zeta)=1-[1-\exp(-\zeta)]/\zeta$ allow the extraction of the particle properties $D=kT/f$, D and $\beta=f/m$ or m from the measured $C(\tau)$ when the data includes values of $\beta\tau\ll 1$, $0.1<\beta\tau<100$ or $\beta\tau\leq 0.1$, respectively, as before. Alternatively, a least-squares or other fit of the measured $C(\tau)$ to Equation (17) can be used to determine D, D and $\beta$ or m directly as in the example computer programs of Appendices B, C and D. In addition, the particle velocity $V_p$ can also be determined from the measured value of the angular bias frequency $\omega=2\pi(V_f-V_p)/\delta$, since $V_f$ and $\delta$ are known and $\omega$ is determined in the measurement of $C(\tau)$.

We also illustrate how the range of values obtainable from $C(\tau)$ can be determined. This determination may be based on two requirements:

1. Sufficient decay of the factor $\exp(-K^2\sigma^2/2)$ must occur over the $\tau$-range for which $C(\tau)$ is measured to allow determination of this decay.

2. The decay of the factor $\exp(-K^2\sigma^2/2)$ must be sufficiently weak so that it can be quantitatively resolved, i.e., the decay must be slow enough to be measured over more than one resolution time or sample time of the correlator.

To insure that these requirements are both satisfied we impose the two conditions $$\exp[-K^2DN\Delta\tau F(\beta N\Delta\tau)]\leq \gamma_1 \quad (18a)$$

$$\exp]-K^2DN_1\Delta\tau F(\beta N_1\Delta\tau)]\leq \gamma_2 \quad (18b)$$

where N is the total number of channels of delay time width $\Delta\tau$ over which the correlation function $C(\tau)$ can be accumulated in a single measurement, $\gamma_1$ is a limiting value sufficiently less than unity so that it can be adequately resolved from unity within the precision of the measured $C(\tau)$ values, $N_1$ are the minimum number of channels of $C(\tau)$ for which values are required to adequately determine D, D and $\beta$, or m and $\gamma_2$ is a limiting value sufficiently greater than zero so that it can adequately resolved from zero within the precision of the measured $C(\tau)$ values. Over the total delay time range for which $C(\tau)$ is determined, $N\Delta\tau$, $\exp(-K^2\sigma^2/2)$ must decay to a value $\leq \gamma_1$. Over the minimum number of channels $N_1$ spanning delay time range $0\leq\tau\leq N_1\Delta\tau$, $\exp(-K^2\sigma^2/2)$ must remain above the value $\gamma_2$.

These two conditions (18a) and (18b) impose lower and upper limits on the range of property values of particle 50 that can be determined by the example method described in this illustration.

For the case when $\beta\tau\leq 0.1$ for which $\sigma^2=kT\tau^2/m$, the range over which m can be determined using the device 10C and correlator at a single set of operating parameter values, such as the value of sample time $\Delta\tau$, fluid temperature T and scattering vector magnitude K, is given by $$K^2kT(N_1\Delta\tau)^2/[2 \ln(1/\gamma_2)]\leq m\leq K^2kT(N\Delta\tau)^2/[2 \ln(1/\gamma_1)] \quad (19a)$$

where $\ln(x)$ denotes the natural logarithm of x. The dynamic mass range which can be measured, or the ratio of maximum to minimum m, is obtained directly from Equation (19a) as $(N/N_1)^2\ln(1/\gamma_2)\ln(1/\gamma_1)$. For the representative values $N=256$, $N_1=12$, $\gamma_1=0.95$ and $\gamma_2=0.05$, the dynamic mass range is 26,580.

For the case when $3\leq\beta\tau$ for which $\sigma^2=2D\tau[1-1/(\beta\tau)]$, the range over which m can be determined (provided $\beta\tau$ is sufficiently small) is given by $$f[N_1\Delta\tau-f \ln(1/\gamma_2)/(K^2kT)]\leq m\leq f[N\Delta\tau-f \ln(1/\gamma_1)/(K^2kT)]. \quad (19b)$$

Because the two parameters f and m are determined in this range of $\beta\tau$, a dynamic mass range and a dynamic range of the friction coefficient are not independently calculated, as in the case of $\beta\tau\leq 0.1$ resulting in Equation (19a). Nevertheless, Equation (19b) allows the selection of operating parameters which provide measurement of the particle property values f and m in their desired ranges and the calculation of the dynamic range in one property given a specified dynamic range of the other.

For the case when $\beta\tau\gg 1$ for which $\sigma^2=2D\tau$, only $D=kT/f$ can be measured. In this case the limits of Equations (18a) and (18b) require $$K^2kTN_1\Delta\tau/\ln(1/\gamma_2)\leq f\leq K^2kTN\Delta\tau/\ln(1/\gamma_1) \quad (19c)$$

from which the dynamic range in f is $(N/N_1)\ln(1/\gamma_2)/\ln(1/\gamma_1)$. For the above defined values of N, $N_1$, $\gamma_1$ and $\gamma_2$, the dynamic range in f is 1,246.

Figure 3:
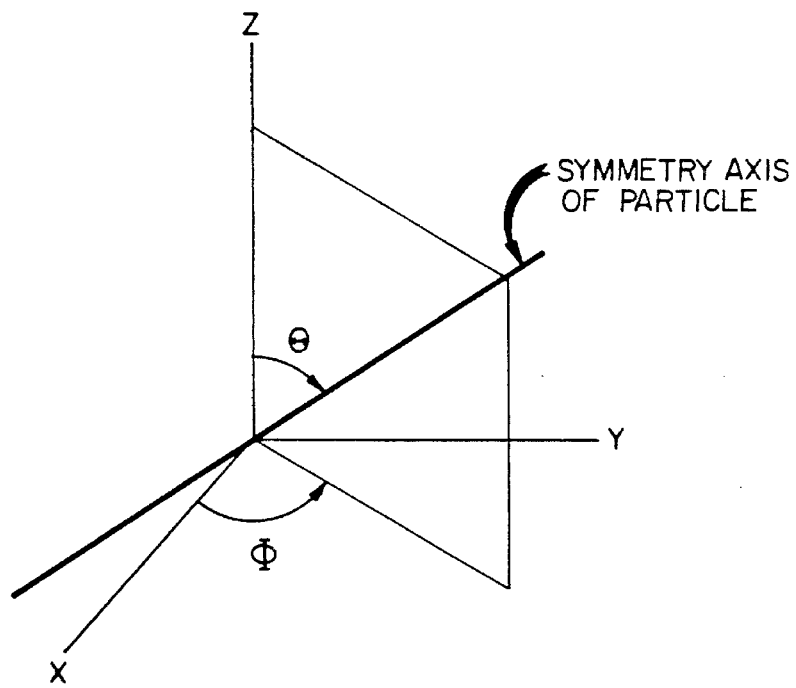
FIG. 3 is a diagram illustrating the orientation of the symmetry axis of an axisymmetric particle in polar coordinates fixed to a laboratory reference frame.

An example analysis of the correlation function of signal $S1(t)$ of device 10B, 10C, 10D or of signal $S_0(t)$ of device 10A, when the time variations of $S_0(t)$ are dominated by rotational motion of particle 50, provides information about particle properties related to particle rotation. Similar to the example analysis above for the signal $S(t)$, fluctuations in time of this signal due, for example, to Brownian rotations of an axisymmetric particle 50 about three mutually perpendicular axes of the signal $S1(t)$ or $S_0(t)$, subject to the stated conditions for $S_0(t)$, gives an analytical expression for the rotational correlation function having the form $$C_r(\tau) = \sum_{j=0}^{\infty} c_j \exp[-j(j+1)\sigma_r^2/2] \quad (20)$$

where the coefficients $c_j$ are constants for any one particle and can be determined empirically. However, it can be shown that for simple systems only a few of the $c_j$ are nonzero at known values of j. Consider, for example, an axisymmetric particle such as rod, disk, spheroid or straight chain aggregate of spheres for all of which only rotation about two axes (those normal to the symmetry axis as shown in FIG. 3 with the polar angle $\Theta$ the inclination of the symmetry axis from the Z axis and $\phi$ the inclination of the x-y plane projection of the symmetry axis from the x axis)

contribute to the fluctuations in light scattered from the particle and $f_r$ and $I_m$ are equal for those two rotational degrees of freedom. By definition, $f_r$ is the rotational friction coefficient of particle 50 for rotation about its axis normal to the symmetry axis and $I_m$ is the mass moment of inertia of the particle about the same axis of rotation. For these simple systems it is possible to fit the measured to the theoretical rotational correlation function $C_r(\tau)$ in order to determine $\sigma_r^2$ at several values of delay time $\tau$. These $\sigma_r^2$ and $\tau$ data pairs can be used with the expression $\sigma_r^2=2D_r\tau F_r(\zeta_r)$ where $D_r=kT/f_r$ with $F_r(\zeta_r)=1-[1-\exp(-\zeta_r)]/\zeta_r$ with $\zeta_r=\beta_r\tau$, and $\beta_r=f_r/I_m$ and $I_m$ the mass moment of inertia of the particle about the same axis of rotation. Thus, for axisymmetric particles or particles adequately approximated by axisymmetric shapes, the particle properties $D_r$ and $I_m$ can be determined from the measured correlation function $C_r(\tau)$. To determine both properties, $\beta_r\tau$ must fall in the range $0.1<\beta_r\tau<100$. For $\beta_r\tau\leq0.1$ only $I_m$ can be determined and for $\beta_r\tau>>1$ only $D_r$.

For the case of rotation of a non-axisymmetric particle the rotational correlation function $C_r(\tau)$ is complex. However, it can be qualitatively represented as the product of two or three functions having the form of Equation (20).

In any case, the comparative forms of the measured rotational correlation function $C_r(\tau)$ and the translational correlation function $C(\tau)$ reveal a general shape category of the particle. Based on results observed for many particle shapes it has been determined that the relative rate of decay of $C_r(\tau)$ is zero for spherical particles, is small for slightly non-spherical particles, moderate for non-spherical particles and large for highly non-spherical particles, where the relative rate of decay in $C_r(\tau)$ is determined by comparison to that of $C(\tau)$ for translational motion.

Morever, analysis of $C_r(\tau)$ can provide information regarding the symmetry of a particle. If the particle is axisymmetric $C_r(\tau)$ can be well fitted by an expression having the form of (18) with $\sigma_r^2$ given by a single set of $f_r$ and $I_m$. When the particle is not axisymmetric, two or three sets of $f_r$ and $I_m$ are required for an adequate fit. Precise data is generally required for such symmetry analysis.

Figure 6:
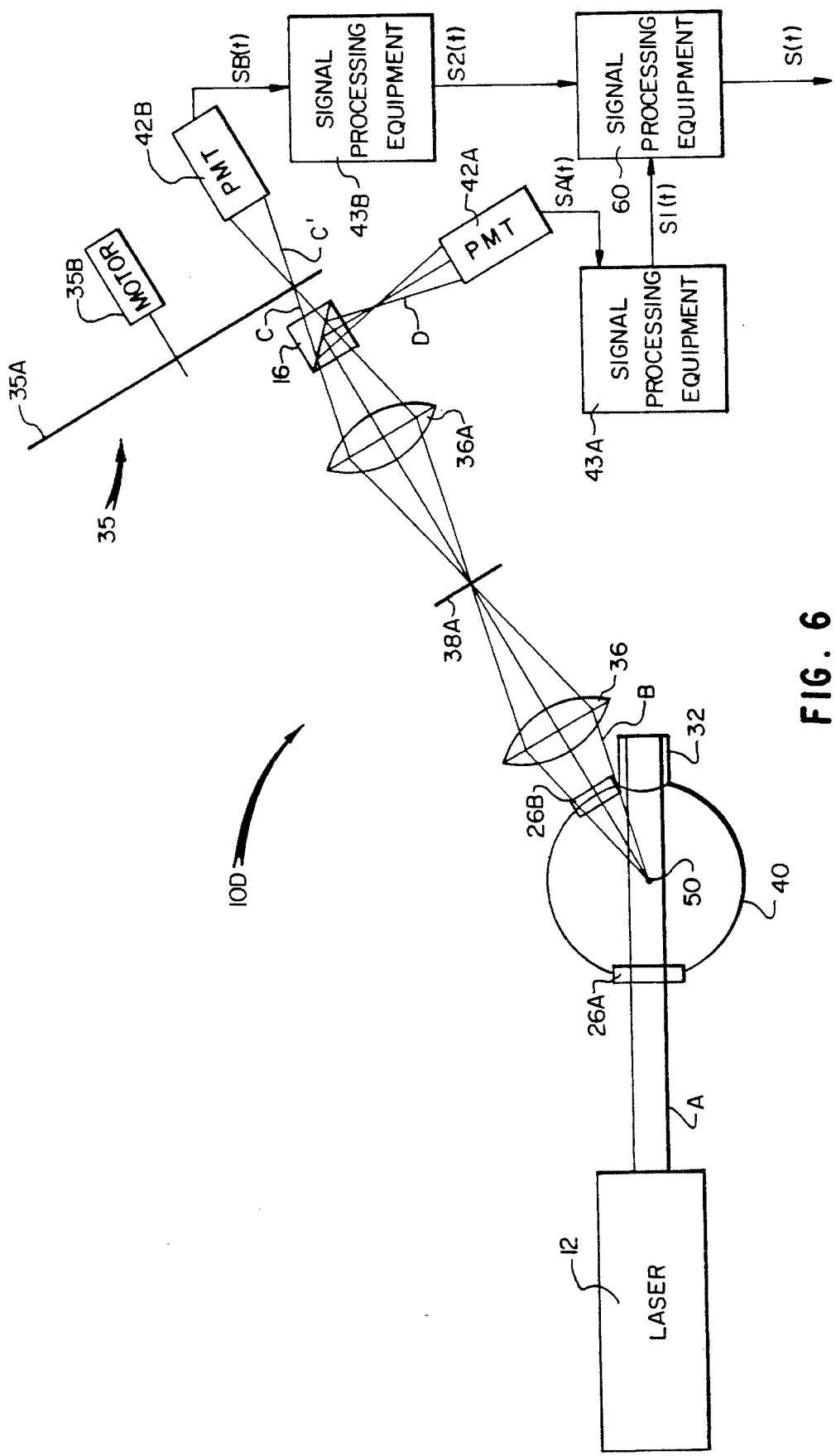
FIG. 6 is a block diagram of an MDLS device having additional features and associated equipment.

In FIG. 6 is shown MDLS device 10D consisting of light or other electromagnetic illumination source 12 which can be, for example, a laser or incandescent light source which generates illumination beam A which passes through window 26A into a sample chamber 40, through the center of chamber 40 and into light trap apparatus 32 at the far side of chamber 40. When at least one particle 50 is located sufficiently near the center of chamber 40, a scattered illumination beam B is generated. The beam B exits chamber 40 through a window 26B, passes through a spatial filter device consisting, for example, of lens 36 and mask 38A having a small aperture near the image plane of the center of chamber 40, through lens 36A, and into beamsplitter 16. The scattered illumination in beam B which passes through the spatial filter device and enters beamsplitter 16 is divided into two beams C and D. Beam C continues through a modulator device 35 consisting, for example, of a finely lined beam chopper disk 35A driven by a motor 35B, onto detector device 42B which may consist of a photomultiplier tube (PMT) which serves to transform the incident scattered illumination signal of modulated beam C' into electrical signal SB(t). Beam chopper 35A is positioned at an image plane of the object plane containing particle 50. As particle 50 displaces due, for example, to random Brownian translations, the location of the image of particle 50 in the plane of beam chopper 35A displaces a corresponding amount, magnified by a magnification M, the magnification in the image plane coincident with chopper 35A due to the optical components of the device. Thus, when particle 50 displaces the distance x(t) normal to the plane of FIG. 6, the image of particle 50 in the image plane located at beam chopper 35A displaces the distance Mx(t), also normal to the plane of FIG. 6 which is the direction of the tangential motion of beam chopper 35A. Modulator device 35 transforms beam C to modulated beam C' by imposing a time and x-direction displacement periodic modulation on the intensity of beam C. When beam chopper 35A is utilized, for example, the scattered illumination of beam C is focused to an image point in the plane of beam chopper 35A and the modulation is imposed by alternately transmitting through and stopping the beam as the transparent and opaque regions associated with each line of the beam chopper traverse the image point location, respectively. Thus, the intensity of scattered illumination in beam C' is modulated periodically in both time t and displacement x(t). The frequency $\Delta F$ of this modulation is given, for example, by the product of the number of lines per revolution $N_r$ of beam chopper 35A and the revolutions per second RPM/60 with which the chopper is rotated.

$$\Delta F = N_r RPM/60 \qquad (21)$$

Table 2 shows example values of $\Delta F$ for selected values of $N_r$ and RPM.

TABLE 2

| $N_r$ | RPM | $\Delta F$, KHz | $N_r$ | RPM | $\Delta F$, KHz |
|-----|------|-------|-----|------|-------|
| 180 | 100  | 0.30  | 360 | 100  | 0.60  |
| 180 | 200  | 0.60  | 360 | 200  | 1.20  |
| 180 | 500  | 1.50  | 360 | 500  | 3.00  |
| 180 | 1000 | 3.00  | 360 | 1000 | 6.00  |
| 180 | 2000 | 6.00  | 360 | 2000 | 12.00 |
| 180 | 5000 | 15.00 | 360 | 5000 | 30.00 |
| 180 | 10000| 30.00 | 360 | 10000| 60.00 |

Beam chopping at sufficiently large radial location on the rotating chopper is preferred so that displacements in the object plane over the field of view allowed by mask 38A result in negligible relative changes in the radial location of the image of particle 50 on the chopper and so that the width of the lines is larger than the image spot size to insure good signal visibility and displacement resolution Beam splitter 16 provides from incident beam B a second output beam D. Beam D is passed onto detector device (PMT) 42A which transforms the incident illumination signal of beam D into electrical signal SA(t). Electric signals SB(t) and SA(t) are processed by signal processing equipment 43B and 43A, respectively, to provide output signals S2(t) and S1(t), respectively. Additional signal processing equipment 60 is used to obtain the signal S(t)=S2(t)/S1(t), time marker signals when the a.c. component of this signal crosses zero amplitude with specified slope, the sequence of time intervals between selected time marker signals, the correlation function of S(t) and other output data. As described above, signal S1(t) is proportional to the product of the instantaneous value of the scattering cross-section of particle 50 and the incident illumination, while signal S2(t) is proportional to this product and also depends on the particle location x(t). The ratio S(t) thus depends only on x(t) and can be used to obtain values of the properties of particle 50 that influence x(t), including the particle mass, translational friction coefficient and velocity component in the x-direction, and information that derives therefrom.

For example, let S(t) be given by the periodic function $g(\Delta\omega t)$ for at least one stationary particle or other scatterer at the center of chamber 40 with $\Delta\omega=2\pi\Delta F$ so that $g(\Delta\omega t)$ can be measured, calculated or controlled by the design and manufacture of chopper 35A. For a non-stationary particle having x-location given by $x(t)=x_O+V_p t+\Delta x(t)$ where $V_p$ is the x-direction velocity of the particle $$S(t)=g(\omega t-K_O M[x_O+\Delta x(t)]) \qquad (22)$$

where $\omega=K_O(V_c-MV_p)$, $V_c=\Delta\omega/K_O$, $K_O=2N_r/d_c$ and $d_c$ is twice the separation of the chopper axis of rotation and the particle image location on chopper 35A. The correlation function of S(t) is then $$C(\tau) = \lim_{L\to\infty} 1/(2L) \int_{-L}^{L} dx0 \int_{-\infty}^{\infty} dx \qquad (23)$$

$$p(x, \tau; -x\hat{O})g(-K_O M x_O)g(\omega\tau - K_O M[x_O + \Delta x(\tau)])$$

where $p(x,\tau;x_O)$ is the transition probability. Once the functions $g(\omega t)$ and $p(x,\tau;x_O)$ are specified, $C(\tau)$ can be determined. Comparison of measured and calculated values of $C(\tau)$ for particles undergoing random Brownian translations, for example, provide values of the translational friction coefficient, mass and x-direction velocity of the particle(s), as illustrated above. When $g(\delta t)=I_O[1+v \cos(\delta\tau)[$, with $I_O$ a constant, the resulting $C(\pi)$ is identical to that given above in Equation (17).

Moreover, when only w is determined from the S(t) or C(τ) data, for example, measured for at least one particle, the velocity of the particle(s) can be obtained from $$V_p=(V_c-\omega/K_O)/M. \qquad (24)$$

When at least one suspended particle is moving with essentially the velocity of the suspending fluid, the local fluid velocity is determined by the value of $V_p$. The device 10D can thus be used to determine the x-direction velocity of a fluid or of at least one particle suspended therein.

When device 10A, 10B, 10C or 10D is used to determine particle translational friction coefficient f, particle mass and x-direction velocity $V_p$ and when an x-direction electrostatic field of magnitude dV/dx is imposed over the intersection volume within chamber 40, the electrostatic charge of the particle is determined by $$q=-fV_p/(dV/dx). \qquad (25)$$

Thus, device 10A, 10B, 10C or 10D can be used to obtain any of the following properties of a particle=mass, translational friction coefficient, x-direction velocity, electrostatic charge, charge to mass ratio (q/m) and shape category.

Information pertaining to chemical composition as obtained by a number of analytical techniques can also be incorporated into the data base for each particle. The light (or other radiation) scattered, transmitted or emitted by the illuminated particle can be used with techniques including emission, Raman, ultraviolet, visible and infrared spectrocopies. Particles such as cells, bacteria, viruses and spores or portions thereof can also be stained to provide a fluorescence signal indicative of a chemical or a biological material. Since fluorescent decay is typically quite fast the detector can monitor the fluctuations in S(t) due to particle translations and rotations by observation of this signal.

Scattered light at a zero scattering angle is isolated from incident illumination in the crossed beam MDLS device by the different directions of the incident and scattered beams and by isolating the a.c. component of the scattered light signal senses to eliminate d.c. components which may be due to non-zero scattering light. Additionally, observation of the forward scattered or emitted light isolated from incident illumination can be used to obtain signals having improved location resolution and signal-to-noise ratios for certain measurements such as light scattering from small particles.

While there has been shown what is considered to be the preferred embodiment of the present invention, it will be manifest that many changes and modifications may be made therein without departing from the essential spirit of the invention. It is intended, therefore, in the annexed claims to cover all such changes and modifications as may fall within the true scope of the invention.

We claim:

1. A method for measuring the radiation scattered or emitted from one or more particles or other sample material at zero or small angle from the forward illumination direction for determining properties of said particles or sample material comprising the steps of:

illuminating said particles or sample material by incident radiation in two crossed beams such that said particles or other sample material are located in the volume over which the beams intersect and a component of the incident radiation has forward direction separated from the axis of either of the two beams of incident radiation;

modulating at least one of said beams so that said component of the incident radiation varies periodically in its intensity with displacement t in time and x in space such that the illumination intensity due to said component is proportional to $\sin(2\pi\Delta Ft-Kx)$ where the modulation frequency $\Delta F$ is the difference in frequency of said two radiation beams and $K=(4\pi/\lambda) \sin(\Psi/2)$ and $\lambda$ the wavelength of the illuminating radiation and $\Psi$ the intersection angle of the two crossed beams;

detecting the scattered or emitted radiation at one or more selected values of scattering angle $\phi$ where $\phi$ is the angle between the forward direction and the axis along which the scattered radiation is detected;

isolating the ac component of the scattered or emitted radiation signal(s) at or near the modulation frequency $\Delta F$; and taking the time-averaged value(s) of the scattered or emitted radiation signal(s) that result from the modulated illumination at said scattering angle(s) to obtain said scattered or emitted radiation signal(s) substantially free of both interference from incident radiation and from uncertainty in illumination radiation intensity due to stationary or slowly varying the spatial variations in space in illumination intensity caused by constructive and destructive interference of the radiation in the intersection volume of the two beams in non-modulated illumination fields or caused by time-averaging of signals over too short a measuring time in non-modulated and slowly modulated illumination fields.

2. An apparatus for measuring the radiation scattered or emitted from one or more particles suspended in a fluid for determining the friction coefficient f=kT/D and/or the mass m of said or more particles comprising:

a. means for generating an electromagnetic radiation field by the intersection of two beams of the electromagnetic radiation at least one of which is modulated to cause the local intensity of the electromagnetic radiation field illuminating the particle to vary periodically with both time and space displacements and utilized to illuminate the particle for a sufficient interval;

b. a detector means for detecting the scattered or emitted radiation from the particle resulting from the illumination for said interval and providing signals relating to the scattered or emitted radiation;

c. signal processing means for processing said signals relating to the scattered or emitted radiation over said interval and providing signals containing measures of mean particle motion and fluctuations about the mean that depend on both the particle mass m or the particle mass and friction coefficient f=k T/D and/or mass m; and d. means for determining f and/or m from said signals containing said measures with k being Boltzmann's constant, T the absolute temperature and D the diffusion coefficient of the particle and with said interval being sufficiently long to provide accurate measures of said mean and said fluctuations about the mean.

3. An apparatus for measuring the radiation scattered from at least one small particle for determining properties of said at least one small particle comprising:

a source of coherent light for generating a first light beam;

means for providing a frequency shift between at least two of said beams; means for dividing said first light beam into at least two light beams;

means for directing two of said light beams along crossed optical paths so as to establish at least one moving fringe pattern within the Intersection of the crossed beams;

at least one sensor means positioned to detect the light scattered by said at least one particle within the intersection of the beams for converting said scattered detected light to at least one signal over the duration of said interval;

at least one signal processing means coupled to said at least one sensor means for receiving the signals therefrom during said interval and for processing said signals to obtain signals containing one or more mean-square-x-displacement $\sigma^2$ values of said particle at one or more values of the time t over which a particle obtains displacement $\Delta x$ and for which $\beta t$ is approximately equal to or less than 0.1; and means for equating the signals containing the measured $\sigma^2$ values to signals containing the theoretical values given by $\sigma^2=ktT^2/m$ so that the mass of said particle is determined by the required condition $m=kTt^2/\sigma^2$ or by the best fit value of m to a number of such conditions for said particle where k is Boltzmann's constant; T is the absolute temperature; D is the diffusion coefficient of the particle; and $\beta$ is equal to f/m, where f is the translational friction coefficient of the particle and m is the mass of the particle and where said interval is sufficiently long to provide sufficiently accurate means of said $\sigma^2$ values to provide a desired accuracy in m.

4. An apparatus for measuring the radiation scattered from small particles for determining properties of said small particles comprising:

a source of coherent light for generating a first light beam;

means for splitting said first light beam into a second and third light beam;

means for splitting said second light beam into a fourth and fifth light beam;

means for providing a frequency shift in said third beam and said fourth beam;

means for recombining said frequency shifted fourth beam and said fifth beam to form a sixth beam;

means for directing said third and sixth beams along crossed optical paths so as to establish a fringe pattern within the intersection of the crossed beams;

at least one sensor means positioned to detect the light scattered by a particle within the intersection of the beams for converting the detected light into a signal containing the measurement of the mean-square-x-displacement $\sigma^2$ value of each particle at one or more values of the time interval t over which a particle obtains displacement $\Delta x$ and for which $\beta t$ is approximately equal to or less than 0.1; and means for equating the signal containing the measured $\sigma^2$ values to a signal containing the theoretical values given by $\sigma^2=kTt^2/m$ so that the mass of each particle is determined by the required condition $m=kTt^2/\sigma^2$ or by the best fit value of m to a number of such conditions for said particles where k is Boltzmann's constant; T is absolute temperature; D is the diffusion coefficient of the particle; and $\beta$ is equal to f/m, where f is the translational friction coefficient of the particle and m is the mass of the particle.

5. An apparatus for measuring the radiation scattered from small particles for determining properties of said small particles comprising:

a source of coherent light for generating a first light beam;

means for splitting said first light beam into a second and a third light beam;

means for splitting said second light beam into a fourth and a fifth light beam;

means for providing a frequency shift in said third beam and said fourth beam;

means for recombining said frequency shifted fourth beam and said fifth beam to form a sixth beam;

a sample chamber;

means for directing said third and said sixth beams along crossed optical paths so as to establish a fringe pattern at the intersection of the crossed beams;

optical means for focusing the light scattered from a particle positioned at the intersection of the crossed beams;

beam splitter means for splitting the light focused by said optical means into two beams that are related to said third and said sixth beams;

at least one sensor means positioned to detect the two beams split by said beam splitter for converting the detected light to obtain a signal containing the measurement of the mean-square-x-displacement $\sigma^2$ value of each particle at one or more values of the time interval t over which a particle obtains displacement $\Delta X$ and for which $\beta t$ is approximately equal to or less than 0.1; and means for equating the signal containing the measured $\sigma^2$ values to a signal containing the theoretical values given by $\sigma^2=kTt^2/m$ so that the mass of each particle is determined by the required condition $m=kTt^2/\sigma^2$ or by the best fit value of m to a number of such conditions for said particles where k is Boltzmann's constant; t is absolute temperature; D is the diffusion coefficient of the particle; and $\beta$ is equal to f/m, where f is the translational friction coefficient of the particle and m is the mass of the particle.

6. An apparatus for measuring the radiation scattered or emitted from one or more particles suspended in a fluid for determining the mass m and/or friction coefficient f of said one or more particles comprising:

a. means for illuminating said one or more particles in an electromagnetic radiation field generated by the intersection of two beams of different frequency to cause said electromagnetic radiation field intensity to vary periodically in both time and space displacements;

b. detector means for detecting the scattered or emitted radiation from said particle(s) resulting from said illumination by said modulated radiation field and for converting the detected scattered or emitted radiation into a signal;

c. means for processing the signal from said detector to obtain a signal containing one or more measured functions of time interval t over which a particle obtains displacement; and d. means for receiving said signal containing the measured function(s) of time interval t and for extracting the values of f=kt/D and/or m for each particle from the signal containing the measured function(s) of time interval t, where k is the Boltzmann's constant, T the absolute temperature of the suspending fluid and D the particle diffusion coefficient.

7. Apparatus according to claim 6, wherein said detector signal has an a.c. component and further including:

a) means for isolating the ac component of the detector signal; and b) means for generating a signal pulse at the times of selected zero crossings in the positive and/or negative going direction of said ac signal component;

c) said signal processing means processing said signal pulses to obtain said one or more measured functions of time interval t.

8. Apparatus for measuring the mass m of one or more particles suspended in a fluid comprising:

a. means for illuminating said one or more particles in an electromagnetic radiation field generated by the intersection of two beams one of which is frequency shifted from the other to cause the intensity of said electromagnetic radiation field to vary periodically in both time and space displacements;

b. a detector means for detecting the scattered or emitted radiation from said particle(s) resulting from said illumination by said modulated radiation field;

c. means for isolating the ac component of the detector signal and for generating signal pulses at the times of selected zero crossings in the positive and/or negative going direction of said ac signal component;

d. means for processing said signal pulses to obtain the distribution p(t) in number of observed zero crossings at time interval t versus time interval t and/or the mean-square-x-displacement $\sigma^2(t)$ at selected values of time interval t where $$p(t)=(2\pi\sigma^2)^{-1/2} \exp[-\Delta x^2/(2\sigma^2)]\delta x$$

with $\Delta x=[\Delta wt-2\pi m_0]/K$ the particle displacement in time interval t between selected zero crossings, $\Delta w$ the angular frequency difference between said two beams, $m_0$ selected integers from the set $0\pm 1, \pm 2, \pm 3, \pm 4, \ldots$ $K=(4\pi/\lambda)\sin(\Psi/2)$ the angular spatial frequency, $\lambda$ the wavelength of said illuminating radiation, $\Psi$ the intersection angle of said two intersecting beams, $\delta x=V_f\delta t$ the resolution in the measurement of displacement $\Delta x$, $V_f=\Delta w/K$ the velocity with which said electromagnetic radiation field is moving, $\delta t$ the resolution in the measurement of time interval t and, for sufficiently small values of t such that $t\leq 0.1/\beta$ with $\beta=f/m$ and f the particle friction coefficient, the mean-square-x-displacement of a particle due to its Brownian motion $\sigma^2(t)=(kT/m)t^2$ with k the Boltzmann's constant and T the absolute temperature of the suspending fluid; and e. means for extracting the values of m of said one or more particles from the measured function(s) p(t) or from values of $\sigma^2(t)$ at one or more selected values of t utilizing the relationship $m=[kT/\sigma^2(t)]t^2$.

9. The method for measuring the radiation scattered from one or more particles in a fluid for determining the mass m and the friction coefficient f of said one or more particles comprising the steps of:

illuminating the particle(s) in a time and space modulated illumination field;

detecting the scattered radiation signal from the particle(s) in said illumination field by use of sensor means that provides a time t dependent electrical signal S(t) in response to the detected scattered radiational signal;

processing said signal S(t) from said sensor means by use of signal processing means to obtain a signal containing processed function $F(\tau)$ with $\tau$ the delay-time or difference in t value between features of interest in S(t) that result in a feature in $F(\tau)$ and with the mathematical form of $F(\tau)$ dependent on the signal processing means utilized;

deriving a signal containing theoretical function $G(\tau,T,D,\beta)$ which corresponds to said function $F(\tau)$ by utilizing the known time and space dependence of the illumination field, the known nature of the signal processing means used and the known distribution of Brownian displacements of the particle(s) which depends on the diffusion coefficient of the particle(s) D=kTF with k Boltzmann's constant and T the absolute temperature of the suspending fluid, on $\beta=f/m$ and on $\tau$;

comparing signals containing the functions $F(\tau)$ and $G(\tau,T,D,\beta)$ for the particle(s) suspended in a fluid at known temperature T at two or more values of the delay-time $\tau$ in order to obtain a signal containing the best fit values of D and $\beta$; and calculating the values of f and m for the particle(s) from said signal containing the best fit values of D and $\beta$ by use of the expressions f=kT/D and $m=\beta/f$.

10. The method of claim 9 wherein:

(1) the illumination field is generated by a pair of crossed laser beams one or both of which are frequency shifted so that the angular frequency difference between the light in the two beams is $\Delta\omega$;

(2) the sensor means is a photo-multiplier tube (PMT);

(3) the signal processing means utilized is autocorrelation;

(4) the function $G(\tau,T,D,\beta)$ is given by $G(\tau,T,D,\beta)=C_o+C_1.\exp[-K^2c^2(\tau)/2].\cos[\Delta\omega\tau]$ with $C_0$ and $C_1$ constants, K the angular spatial frequency given by $4n/\lambda_o\sin[\Psi/2]$, $\Delta\omega$ the angular bias frequency and $\sigma^2(\tau)$ the mean-square-x-displacement of the particle(s) in delay-time $\tau$ given by $2D\tau F(\beta\tau)$ where D=kT/f, k is the Boltzmann's constant, T the absolute fluid temperature, f the friction coefficient of the particle(s), $\beta=f/m$ and $F(\beta\tau)=1-[1-\exp(-\beta\tau)]/(\beta\tau)$.

11. The method of claim 9 wherein:

(1) the illumination field is generated by a pair of crossed laser beams one or both of which are frequency shifted so that the angular frequency difference between the light in the two beams is $\Delta\omega$;

(2) the sensor means is a photo-multiplier tube (PMT);

(3) the signal S(t) is provided by circuitry means that produces narrow voltage pulses at the times the ac component of the signal from said PMT crosses zero in the positive going direction for the $m_o$-lth time following the previous pulse with $m_o$ selected from 1, 2, 3, 4, 5, 6 . . . ;

(4) the signal processing means utilized is autocorrelation so that $F(\tau)$ is the probability density in delay-time $\tau$ of said pulses and said positive going zero crossings;

(5) the function $G(\tau,T,D,\beta)$ is given by $G(\tau,T,D,\beta)-(2\pi\sigma^2)^{-1/2}\Delta\omega\exp[-(\Delta w-2m_0\pi)^2/(2\sigma^2)]$ with a $(\sigma^2\tau)$ the mean-square-x-displacement of the particle(s) in delay-time $\tau$ given by $2D\tau F(\beta\tau)$ where $D=kT/f$, k is the Boltzmann's constant, T the absolute fluid temperature, f the friction coefficient of the particle(s), $\beta=f/m$ and $F(\beta\tau)=1-[1-\exp(-\beta\tau)]/(\beta\tau)$ and with K the angular spatial frequency given by $4n_r/\lambda_0 \sin[\Psi/2]$, $\Delta\omega$ the angular bias frequency and $m_0$ selected from the values 1, 2, 3, 4, 5, 6 . . . .

12. A method for measuring the radiation scattered or emitted from one or more particles in a fluid for determining the mass m of said one or more particles comprising the steps of:

illuminating the particle(s) with a time and space modulated illumination field;

sensing the magnitude of the scattered or emitted signal from the particle(s);

utilizing said magnitude of said scattered or emitted signal to provide a signal containing the mean-square-x-displacement $\sigma^2$ value of one or more particles at one or more values of time t for which $\beta t$ is approximately equal to or less than 0.1 where $\beta=f/m$ with f the friction coefficient of the particle and m the particle mass; and equating the signal containing said $\sigma^2$ value at said one or more values of time t to a signal containing the theoretical value(s) given by $\sigma^2=kTt^2/m$ so that the mass of said particle(s) is determined by the required condition $m=kTt^2/\sigma^2$ or by the best fit value of m to a number of such conditions for said particle(s) with k the Boltzmann's constant and T the absolute temperature of the suspending-fluid.

13. A method for measuring the radiation scattered or emitted from one or more particles in a fluid for determining both the friction coefficient f and mass m of said one or more particles comprising the steps of:

illuminating the particle(s) with a time and space modulated illumination field;

sensing the magnitude of the scattered or emitted signal from the particle(s);

utilizing the magnitude of the scattered or emitted signals to provide a signal containing the mean-square-x-displacement $\sigma^2$ values of one or more particles at two or more values of time t for which $\beta t$ is approximately equal to or less than 100 where $\beta=f/m$ and equating the signal containing said $\sigma^2$ values at said two or more given values of time t to a signal containing the theoretical values given by $\sigma^2=2kTt/f\, F(\beta t)$ where k is the Boltzmann's constant, T is the absolute temperature of said fluid and $F(\beta t)=1-[\exp(-\beta t)]/(\beta t)$ so that the friction coefficient and mass of particle(s) are determined by the required conditions $F(\beta t)/f=\sigma^2/(2kTt)$ for the two said $\sigma^2(t)$ and t data pair values or so that the best fit values of friction coefficient and mass of said particle(s) are determined by the required conditions $F(\beta t)/f=\sigma^2/(2kTt)$ for the three or more said $\sigma^2(t)$ and t data pair values.

14. The method for measuring the radiation scattered or emitted from one or more particles for determining particle friction coefficient f and/or mass m according to claim 13 wherein the mean-square-x-displacement $\sigma^2$ values at to or more values of delay-time are determined by the steps of:

illuminating the particle(s) with a time and space modulated illumination field;

sensing the magnitude of the scattered or emitted signal S(t) from the particle(s);

computing the autocorrelation function $C(\tau)=<S(t)S(t+\tau)>$ of said scattered or emitted signal where $\tau$ is the delay-time variable and the angular brackets indicate the average over time t of the enclosed quantity; and comparing a signal containing said computed autocorrelation function to a signal containing the theoretical autocorrelation function containing the factor $C(\tau)=\alpha^2 [1+=v^2/2 \exp(-K^2\tau^2/2) \cos(\omega\tau)]$ where $\alpha$ and v are constants and K is the known magnitude of the scattering vector and $\omega$ is the constant angular frequency to determine said mean-square-x-displacement $\sigma^2(\tau)$ versus $\tau$.

15. The method for determining particle friction coefficient f and/or mass m according to claim 13 wherein the mean-square-x-displacement $\sigma^2$ values at two or more values of delay-time are determined by the steps of;

illuminating the particle(s) with a time and space modulated illumination field;

sensing the magnitude of the scattered or emitted signal S(t) from the particle(s);

filtering said signal S(t) using a high-pass filter so that DC and low frequency components of S(t) are removed and only high frequency components having frequency greater than approximately one-tenth the bias frequency are retained in the residual signal $S_1(t)$;

detecting the times of selected zero crossings of said residual signal $S_1(t)$;

computing the delay times of selected pairs of zero crossings given by the magnitudes of the differences between selected pairs of zero crossing times and/or the corresponding particle displacements that occur over the delay time intervals given in each case by $\Delta X-[\Delta\omega\tau-2n\pi]/K$ where $\Delta\omega$ is the bias frequency and $\tau$ is the delay time and n is the value determined from the number of zero crossings between said pair of selected zero crossings;

computing the probability density in delay time $\tau p(\tau)$ of said selected zero crossings and/or the probability density in particle displacement $\Delta x\, p(\Delta x)$ of said selected zero crossings; and determining the value(s) of $\sigma^2$ at one or more values of $\tau$ by comparison of said computed probability density p($\tau$) to the theoretical expression given by $p(\tau)=(2\pi\tau^2)^{-1/2}V_f \exp[-(V_f\tau-2n\pi/K)^2/(2\sigma^2)]$ where $V_f$ is the x-direction velocity of any feature of the modulated illumination field and/or by comparison of said probability density p($\Delta x$) to the theoretical expression given by $p(\Delta x)=(2\pi\sigma^2)^{-1/2} \exp[-\Delta x^2/(2\sigma^2)]$.

16. A method for measuring the radiation scattered or emitted from one or more particles in a fluid for determining the friction coefficient f and/or mass m of said one or more particles comprising the steps of;

illuminating the particle(s) with a time and space modulated illumination field;

sensing the magnitude of the scattered or emitted signal from the particle(s);

utilizing said magnitude of said scattered or emitted signal to provide a signal containing the mean-square-x-displacement $\sigma^2$ values of one or more particles at two or more values of time t for which $\beta t$ is approximately equal to or less than 100 where $\beta-f/m$ with f the particle friction coefficient and m the particle mass; and equating the signal containing said $\sigma^2$ values at said two or more values of time t to a signal containing the theoretical values given by $\sigma^2=2kTt/f \cdot F(\beta t)$ where $F(\beta t)=1-[1-\exp(-\beta t)]/(\beta t)$ so that the friction coefficient and mass of said particle(s) are determined by the required conditions $F(\beta t)/f=\sigma^2/(2kTt)$ for the two said $\sigma^2(t)$ and t data pair values or so that the best fit values of friction coefficient and mass of said particle(s) are determined by the required conditions $F(\beta)/f=\sigma^2/(2kTt)$ for the three or more said $\sigma^2(t)$ and t data pair values where k is the Boltzmann's constant and T the absolute temperature of the suspending fluid.

17. An apparatus for measuring radiation scattered by small particles for determining properties of said small particles comprising:

a source of coherent light for generating a first light beam;

means for dividing said first light beam into at least two light beams;

means for providing a frequency shift between at least two of said beams;

means for directing said at least two frequency shifted light beams along crossed optical paths so as to establish at least one fringe pattern within the intersection of the crossed beams;

at least one sensor means positioned to detect the light scattered by a particle within the intersection of the beams for converting at least one detected light to at least one signal;

at least one signal processing means coupled to at least one said sensor means for receiving the signals therefrom and for processing said signals to obtain a signal containing the autocorrelation found in $C(\tau)=<S(t)S(t+\tau)>$ and to determine therefrom the particle friction coefficient f and/or the particle mass m and/or the particle velocity $V_p$ in accordance with the following:

$$C(\tau)=\alpha^2[1+\gamma^2/2 \exp(-k^2\sigma^2/2) \cos(\omega\tau)]$$

by obtaining a signal containing the best fit values $\omega$, $\alpha^2$, $\gamma^2$ and $\sigma^2(t)$ vs. t from the measured values of C(t) vs. t and the known values of $K^2$, Vf and $\sigma$ and using the relationship:

$$\sigma^2=2DtF(\beta t),\ V_{p=vp}V_f-\omega/K,\ f=kT/D,\ \text{and}\ \beta=f/m$$

where $\tau$ is the time delay, $\alpha$ is an instrument constant, $\gamma$ is the visibility of the particle in the fringe field, K is the magnitude of the scattering vector, $\sigma^2$ is the particle mean square displacement, $\omega$ is the angular bias frequency given by $\omega=2\pi(V_f-V_p)/\delta$ where Vf is the fringe field velocity given by $V_f=\Delta\omega/k$ and $\delta$ is the fringe period given by $\delta=2\pi/K$, D is the diffusion coefficient of the particle, k is Boltzman's constant and T is the absolute temperature.

* * * * *

UNITED STATES PATENT AND TRADEMARK OFFICE
CERTIFICATE OF CORRECTION

PATENT NO. : 5,502,561
DATED : March 26, 1996
INVENTOR(S) : D K. Hutchins, et al It is certified that error appears in the above-indentified patent and that said Letters Patent is hereby corrected as shown below:

Column 19, Line 50 of Patent should read -- sufficiently long to provide sufficiently accurate measures --

Column 22, Line 28 of Patent should read -- diffusion coefficient of the particle(s) DkTF with k --

Column 22, Line 50 of Patent should read -- $\lambda_0 \sin[\gamma/2]$, $\Delta\omega$ the angular bias frequency and $\sigma^2(\tau)$ --

Column 24, Lines 3-4 of Patent should read -- computing the autocorrelation function $C(\tau)<S(t)S(t+\tau)>$ of said scattered or emitted signal where $\tau$ is the --

Column 24, Lines 9-10 of Patent should read -- autocorrelation function containing the factor $C(\tau) = \alpha^2[1+v^2/2 \exp(-K^2\sigma^2/2) \cos(\omega\tau)]$ where $\alpha$ and v are --

Column 24, Line 45 of Patent should read -- $(\tau)$ to the theoretical expression given by $p(\tau) = (2\pi\sigma^2)^{-}$ --

Column 24, Line 64 of Patent should read -- equal to or less than 100 where $\beta$ = f/m with f the particle --

Column 26, Line 15 of Patent -- $\sigma^2 = 2DtF(\beta t)$, $V_p = V_f - \omega/K$, $f = kT/D$, and $\beta = f/m$ --

Signed and Sealed this

Seventeenth Day of December, 1996

Attest:

BRUCE LEHMAN

*Attesting Officer*  *Commissioner of Patents and Trademarks*